US008412321B2

(12) United States Patent
Gilmour, Jr. et al.

(10) Patent No.: US 8,412,321 B2
(45) Date of Patent: *Apr. 2, 2013

(54) METHOD OF IDENTIFYING STRATEGIES FOR TREATMENT OR PREVENTION OF VENTRICULAR FIBRILLATION AND VENTRICULAR TACHYCARDIA

(75) Inventors: Robert Gilmour, Jr., Ithaca, NY (US); Jeffrey J. Fox, Ithaca, NY (US); Mark Riccio, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/787,578

(22) Filed: May 26, 2010

(65) Prior Publication Data

US 2010/0233088 A1 Sep. 16, 2010

Related U.S. Application Data

(62) Division of application No. 10/588,395, filed as application No. PCT/US2005/002848 on Feb. 2, 2005, now Pat. No. 7,818,055.

(60) Provisional application No. 60/541,531, filed on Feb. 3, 2004.

(51) Int. Cl.
*A61N 1/39* (2006.01)
(52) U.S. Cl. ........................................................ 607/5
(58) Field of Classification Search .................. 600/508; 607/27
See application file for complete search history.

(56) References Cited

U.S. PATENT DOCUMENTS

| 5,824,018 | A  | 10/1998 | Dreher et al. |
| 6,847,843 | B1 | 1/2005  | Mouchawar et al. |
| 2004/0215242 | A1 | 10/2004 | Van Dalen |
| 2004/0220640 | A1 | 11/2004 | Burnes et al. |
| 2005/0059897 | A1 | 3/2005  | Snell et al. |
| 2007/0043395 | A1 | 2/2007  | Wei et al. |

OTHER PUBLICATIONS

Fox et al., "Period-Doubling Instability and Memory in Cardiac Tissue," Phys Rev Lett 89(13):138101-1-138101-4 (2002).
Fox et al., "Conduction Block in One-Dimensional Heart Fibers," Phys Rev Lett 89(19):198101-1-198101-4 (2002).
Fox et al., "Spatiotemporal Transition to Conduction Block in Canine Ventricle," Circ Res 90:289-296 (2002).
Fox et al., "Dynamic Mechanism for Conduction Block in Heart Tissue," New J. Phys. 5:1.1-1.14 (2003).
Fox et al., "Dynamic Mechanism for Conduction Block in Cardiac Tissue," Oral Presentation at the SIAM Conference, Montreal, Canada (Jun. 19, 2003).
Gilmour, Robert F., "A Novel Approach to Identifying Antiarrhythmic Drug Targets," DDT 8(4):162-67 (2003).

*Primary Examiner* — Carl H Layno
*Assistant Examiner* — Allen Porter, Jr.
(74) *Attorney, Agent, or Firm* — LeClairRyan, a Professional Corporation

(57) ABSTRACT

The present invention relates to evaluating the effect of physiological conditions on the occurrence of ventricular fibrillation, identifying strategies for treatment or prevention of ventricular fibrillation or ventricular tachycardia, and evaluating a subject for induction of ventricular fibrillation from a condition of ventricular tachycardia.

6 Claims, 27 Drawing Sheets

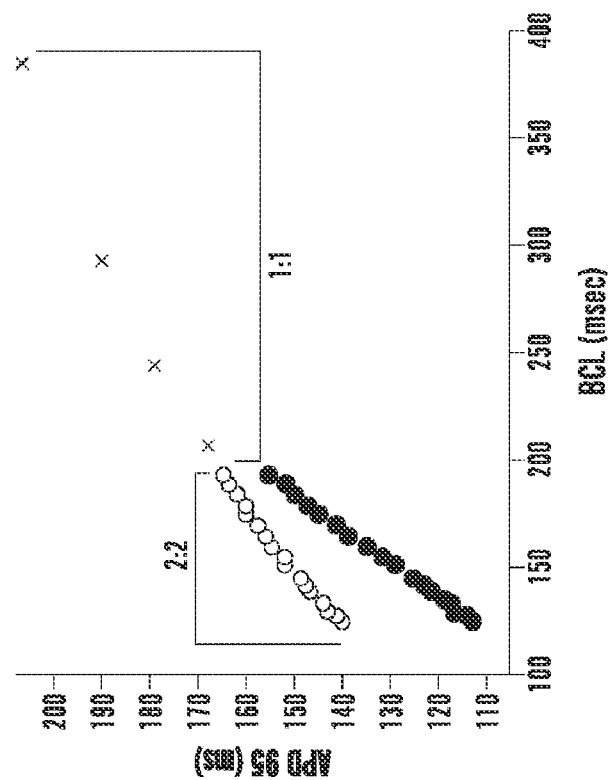
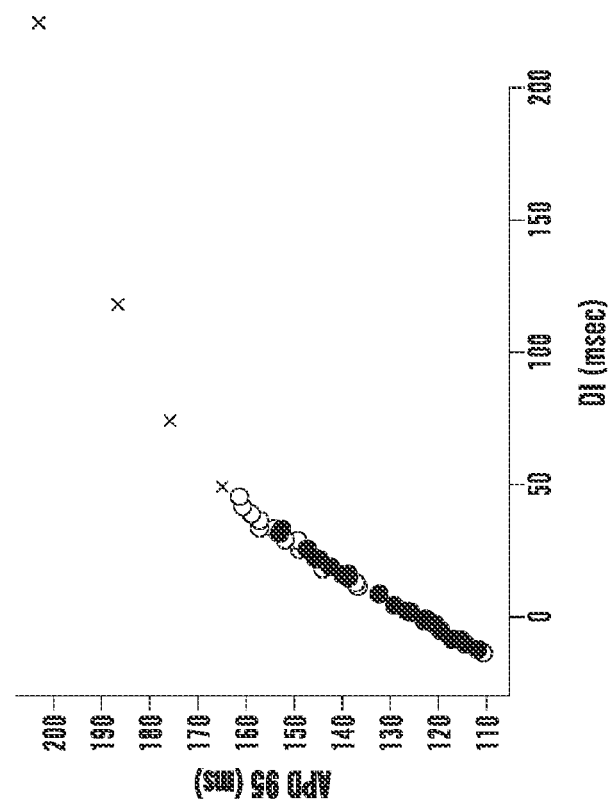

US 8,412,321 B2

METHOD OF IDENTIFYING STRATEGIES FOR TREATMENT OR PREVENTION OF VENTRICULAR FIBRILLATION AND VENTRICULAR TACHYCARDIA

This application is a divisional application of U.S. patent application Ser. No. 10/588,395, filed Jun. 29, 2007, now U.S. Pat. No. 7,818,055, issued Oct. 19, 2010, which is a national stage application, under 35 U.S.C. §371 from PCT Application No. PCT/US2005/002848, filed Feb. 2, 2005, which claims priority benefit of U.S. Provisional Patent Application Ser. No. 60/541,531, filed Feb. 3, 2004, which is hereby incorporated by reference in its entirety.

This application was made, at least in part, with funding received from the National Institutes of Health under Contract No. HL62543. The U.S. government has certain rights in this invention.

FIELD OF THE INVENTION

The present invention relates to a method of identifying strategies for the treatment or prevention of ventricular fibrillation and ventricular tachycardia.

BACKGROUND OF THE INVENTION

Catastrophic heart rhythm disorders are among the leading causes of death in the United States. The most dangerous of these arrhythmias is ventricular fibrillation, a disturbance in which disordered wave propagation causes a fatal disruption of the synchronous contraction of the ventricle. Although the exact mechanism for fibrillation is still being debated, one theory proposes that fibrillation is a state of spatiotemporal chaos consisting of the perpetual nucleation and disintegration of spiral waves (Chen et al., "Mechanism of Ventricular Vulnerability to Single Premature Stimuli in Open-Chest Dogs," *Circ Res* 62:1991-209 (1988) and Witkowski et al., "Spatiotemporal Evolution of Ventricular Fibrillation," *Nature* 392:78-82 (1998)), in association with a period doubling bifurcation of local electrical properties (Garfinkel et al., "Preventing Ventricular Fibrillation by Flattening Cardiac Restitution," *Proc Natl Acad Sci USA* 97:6061-6 (2000); Gilmour et al., "Electrical Restitution, Critical Mass, and the Riddle of Fibrillation," *J Cardiovasc Electrophysiol* 10:1087-9 (1999); Karma, A., "Electrical Alternans and Spiral Wave Breakup in Cardiac Tissue," *Chaos* 4:461-72 (1994); and Panfilov, A., "Spiral Breakup as a Model of Ventricular Fibration," *Chaos* 8:57-64 (1998)). Nucleation of the initiating spiral wave pair is caused by local conduction block (wave break) secondary to spatial heterogeneity of refractoriness in the ventricle (Arce et al., "Alternans and Higher-Order Rhythms in an Ionic Model of a Sheet of Ischemic Ventricular Muscle," *Chaos* 10:411-26 (2000); Chen et al., "Mechanism of Ventricular Vulnerability to Single Premature Stimuli in Open-Chest Dogs," *Circ Res* 62:1991-209 (1988); Sampson et al., "Simulation and Prediction of Functional Block in the Presence of Structural and Ionic Heterogeneity," *Am J Physiol* 281:H2597-603 (2001); Winfree, *When Time Breaks Down* (Princeton, N.J.: Princeton University Press) (1987); and Witkowski et al., "Spatiotemporal Evolution of Ventricular Fibrillation," *Nature* 392:78-82 (1998)). Until recently, spatial heterogeneity was thought to result solely from regional variations of intrinsic cellular electrical properties (Sampson et al., "Simulation and Prediction of Functional Block in the Presence of Structural and Ionic Heterogeneity," *Am J Physiol* 281:H2597-603 (2001); and Yan et al., "Characteristics and Distribution of M Cells in Arterially Perfused Canine Left Ventricular Wedge Preparations," *Circulation* 98:1921-7 (1998)) or from stimulation at more than one spatial location (Qu et al., "Mechanisms of Discordant Alternans and Induction of Reentry in Simulated Cardiac Tissue," *Circulation* 102:1664-70 (2000); Watanabe et al., "Mechanisms for Discordant Alternans," *J Cardiovasc Electrophysiol* 12:196-206 (2001); and Winfree, *When Time Breaks Down* (Princeton, N.J.: Princeton University Press) (1987)). However, it is now appreciated that purely dynamical heterogeneity can be sufficient to cause conduction block during single-site stimulation in both homogeneous one-dimensional models of canine heart tissue and in rapidly paced canine Purkinje fibres (Echebarria et al., "Instability and Spatiotemporal Dynamics of Alternans in Paced Cardiac Tissue," *Phys Rev Lett* 88:208101 (2002) and Fox et al, "Spatiotemporal Transition to Conduction Block in Canine Ventricle," *Circ Res.* 90:289-96 (2002)). A similar mechanism has been shown to precipitate conduction block and spiral break-up in models of homogeneous two-dimensional tissue (Fenton et al., "Multiple Mechanisms of Spiral Wave Breakup in a Model of Cardiac Electrical Activity," *Chaos* 12:852-92 (2002)).

The period doubling bifurcation implicated in the transition to conduction block is manifest as alternans, a beat-to-beat long-short alternation in the duration of the cardiac action potential (Garfinkel et al., "Preventing Ventricular Fibrillation by Flattening Cardiac Restitution," *Proc Natl Acad Sci USA* 97:6061-6 (2000); Gilmour et al., "Electrical Restitution, Critical Mass, and the Riddle of Fibrillation," *J Cardiovasc Electrophysiol* 10:1087-9 (1999); Karma, A., "Electrical Alternans and Spiral Wave Breakup in Cardiac Tissue," *Chaos* 4:461-72 (1994); Panfilov, A., "Spiral Breakup as a Model of Ventricular Fibration," *Chaos* 8:57-64 (1998); and Watanabe et al., "Mechanisms for Discordant Alternans,"*J Cardiovasc Electrophysiol* 12:196-206 (2001)). Previous investigators have hypothesized that alternans can be accounted for by a simple uni-dimensional return map called the action potential duration restitution function (Chialvo et al., "Low Dimensional Chaos in Cardiac Tissue," *Nature* 343:653-7 (1990); Chialvo et al., "Non-Linear Dynamics of Cardiac Excitation and Impulse Propagation," *Nature* 330:749-52 (1987); Guevara et al., "Electrical Alternans and Period Doubling Bifurcations," *IEEE Comput Cardiol* 562:167-70 (1984); and Nolasco et al., "A Graphic Method for the Study of Alternation in Cardiac Action Potentials," *J Appl Physiol* 25:191-6 (1968)). This hypothesis assumes the duration D of an action potential depends only on its preceding rest interval I through some function $f(I)$ that is measured experimentally. If the D restitution function has a slope $\geq 1$, then a period doubling bifurcation occurs for some value of the stimulus period T, where $T=D+I$. The velocity V at which an action potential propagates can also be described by a restitution function, where $V=c(I)$.

It has also been shown previously that the combination of a steeply sloped action potential duration ("APD") restitution function and a monotonically increasing conduction velocity ("CV") restitution function is sufficient to produce dynamical conduction block during sustained pacing at a short cycle length (Fox et al, "Conduction Block in One-dimensional heart Fibers," *Phys. Rev. Lett.* 89:198101 (2002); Fox et al, "Spatiotemporal Transition to Conduction Block in Canine Ventricle," *Circ. Res.* 90:289-96 (2002)). This observation may provide a generic mechanism for wave break and the onset of ventricular tachycardia and fibrillation. However, it is unlikely that the conditions used to demonstrate this phenomenon experimentally apply to the clinical situation, where the induction of ventricular tachyarrhythmias typically is associated with the interruption of normal cardiac rhythm by only a few premature beats. A single premature beat is sufficient to cause spatial heterogeneity in the form of discordant alternans (Watanabe et al., "Mechanisms for Discordant Alternans," *J Cardiovasc Electrophysiol* 12:196-206 (2001)), but the conditions required for the development of conduction block in this setting have not been studied extensively.

Other studies, building on earlier theoretical work by Krinsky, Winfree and colleagues (Krinsky et al, "Votices with Linear Cores in Mathematical Models of Excitable Media," *Physica A* 188:55-60 (1992) and Winfree, A., "Evolving Perspectives During 12 Years of Electrical Turbulence," *Chaos* 8:1-20 (1998)) and experiments by Allessie (Allessie et al., "Circus Movement in Rabbit Atrial Muscle as a Mechanism of Tachycardia. III. The 'Leading Circle' Concept: a New Model of Circus Movement in Cardiac Tissue Without the Involvement of an Anatomical Obstacle," *Circ Res* 41:9-18 (1977)), have suggested that spiral wave re-entry could be the 'engine' that drives ventricular fibrillation ("VF") (Frazier et al., "Stimulus-Induced Critical Point. Mechanism for Electrical Initiation of Reentry in Normal Canine Myocardium," *J Clin Invest* 83:1039-1052 (1989); Witkowski et al., "Spatiotemporal Evolution of Ventricular Fibrillation," *Nature* 392:78-82 (1998); Weiss et al., "Chaos and the Transition to Ventricular Fibrillation: a New Approach to Antiarrhythmic Drug Evaluation," *Circulation* 99:2819-2826 (1999); Chen et al., "Mechanism of Ventricular Vulnerability to Single Premature Stimuli in Open-Chest Dogs," *Circ Res* 62:1191-1209 (1988); Gilmour et al., "Electrical Restitution, Critical Mass, and the Riddle of Fibrillation," *J Cardiovasc Electrophysiol* 10:1087-1089 (1999); and Pertsov et al., "Spiral Waves of Excitation Underlie Reentrant Activity in Isolated Cardiac Muscle," *Circ Res* 72:631-650 (1993)). Although there is substantial evidence that spiral wave re-entry contributes significantly to the induction and maintenance of VF, the exact mechanisms by which spiral waves sustain VF is currently being debated.

The present invention is directed towards correctly identifying the mechanisms (or more likely, mechanisms) by which spiral waves cause VF and the development of pharmacological approaches to VF treatment and prevention.

SUMMARY OF THE INVENTION

The present invention relates to a method of evaluating the effect of a physiological condition on the occurrence of ventricular fibrillation. This method involves providing a test system and initiating a ventricular fibrillation inducing sequence in the test system by interrupting normal sinus heart rhythm with premature electrical stimuli. Following the initiation of ventricular fibrillation a ventricular recovery sequence is initiated. The test system is subjected to a physiological condition before, during, and after initiating the ventricular fibrillation recovery sequence and the physiological conditions which affect ventricular fibrillation recovery are identified.

Another aspect of the present invention relates to method of identifying treatment candidates as therapeutic strategies for the prevention of ventricular fibrillation. This method involves providing a test system and initiating a ventricular fibrillation inducing sequence in the test system by interrupting normal sinus heart rhythm with premature electrical stimuli before, during, and after administering the treatment candidate to the test system. Treatment candidates which prevent the initiation step from inducing ventricular fibrillation are identified as therapeutic strategies for prevention of ventricular fibrillation.

A further aspect of the present invention relates to a method of identifying treatment candidates as therapeutic strategies for treating ventricular fibrillation. This method includes providing a test system and initiating a ventricular fibrillation inducing sequence in the test system by interrupting normal sinus heart rhythm with premature electrical stimuli, resulting in ventricular fibrillation in the test system. Treatment candidates are administered to the test system undergoing ventricular fibrillation and treatment candidates which modulate ventricular fibrillation are identified as therapeutic strategies for treatment of ventricular fibrillation.

The present invention also relates to a method of evaluating the predisposition of a subject for the induction of ventricular fibrillation from a condition of ventricular tachycardia. This method involves providing a subject in ventricular tachycardia and monitoring the electrical stimuli in the heart of the subject. It is then determined if a sequence of rest interval values correspond to rest interval values predicted to lead to ventricular fibrillation consistent with the histogram of FIG. 7.

Another aspect of the present invention relates to a method of identifying treatment candidates as therapeutic strategies for preventing ventricular tachycardia from developing into ventricular fibrillation. This involves providing a subject in ventricular tachycardia and monitoring the electrical stimuli in the heart of the subject. It is then determined if the initial 3 stimuli in groups of 4 stimuli correspond to rest interval values predicted to lead to ventricular fibrillation consistent with the histogram of FIG. 7. Treatment candidates which prevent occurrence of a fourth stimuli corresponding to a rest interval value predicted to lead to ventricular fibrillation consistent with the histogram of FIG. 7 are identified. Treatment candidates which prevent ventricular tachycardia from becoming ventricular fibrillation are identified as therapeutic strategies for preventing ventricular fibrillation.

One of the hypotheses to account for the apparent link between spiral waves and VF is the restitution hypothesis, which proposes that VF is caused by the breakup of a single spiral wave into multiple self-perpetuating wavelets (Weiss et al., "Chaos and the Transition to Ventricular Fibrillation: a New Approach to Antiarrhythmic Drug Evaluation," *Circulation* 99:2819-2826 (1999); Gilmour et al., "Electrical Restitution, Critical Mass, and the Riddle of Fibrillation," *J Cardiovasc Electrophysiol* 10:1087-1089 (1999); Garfinkel et al., "Preventing Ventricular Fibrillation by Flattening Cardiac Restitution," *Proc Natl Acad Sci USA* 97:6061-6066 (2000); Riccio et al., "Electrical Restitution and Spatiotemporal Organization During Ventricular Fibrillation," *Circ Res* 84:955-963 (1999); Panfilov et al., "Ventricular Fibrillation: Evolution of the Multiple Wave Hypothesis," *Philos Trans R Soc Lond Ser A* 359:1315-1325 (2001); Fenton et al., "Multiple Mechanisms of Spiral Wave Breakup in a Model of Cardiac Electrical Activity," *Chaos* 12:852-892 (2002); Karma, A., "Spiral Breakup in Model Equations of Action Potential Propagation in Cardiac Tissue," *Physc Rev Lett* 71:1103-1106 (1993); and Karma, A., "Electrical Alternans and Spiral Wave Breakup in Cardiac Tissue," *Chaos* 4:461-472 (1994), which are hereby incorporated by reference in their entirety). This mechanism is similar to that proposed decades ago by Moe (Moe, G., "A Computer Model of Atrial Fibrillation," *Am Heart J* 67:200-220 (1964), which is hereby incorporated by reference in its entirety), but with one important difference: it may occur in intrinsically homogeneous cardiac tissue. The transition from normal planar wave excitation to a single spiral wave and ultimately to multiple wavelets is thought to underlie the transition from normal sinus rhythm to ventricular tachycardia and VF characteristic of patients who succumb to sudden death (FIG. 1).

The exact mechanism for the breakup of spiral waves is unknown. However, there is considerable evidence that breakup is closely related to APD restitution, which is the relationship between action potential duration (APD) and diastolic interval (DI, the time interval between action potentials), where APD is determined by the preceding DI (FIG. 2). During pacing of cardiac tissue at progressively shorter cycle lengths, APD decreases, until at sufficiently short cycle lengths a period doubling bifurcation occurs and APD begins to alternate between a long duration and a short duration, a phenomenon known as APD alternans (FIG. 2) (Moe, G., "A Computer Model of Atrial Fibrillation," *Am Heart J* 67:200-220 (1964) (Guevara et al., "Electrical Alternans and Period Doubling Bifurcations," *IEEE Comp Cardiol* 562:167-170 (1984); Chialvo et al., "Low Dimensional Chaos in Cardiac Tissue," *Nature* 343:653-657 (1990); Karagueuzian et al., "Action Potential Alternans and Irregular Dynamics in Quinidine-Intoxicated Ventricular Muscle Cells. Implications for Ventricular Proarrhythmia," *Circulation* 87:1661-1672 (1993); Nolasco et al., "A Graphic Method for the Study of Alternation in Cardiac Action Potentials," *J Appl Physiol* 25:191-196 (1968); Rosenbaum et al., "Electrical Alternans and Vulnerability to Ventricular Arrhythmias," *New Engl J Med* 330:235-241 (1994); Pastore et al., "Mechanism Linking T-Wave Alternans to the Genesis of Cardiac Fibrillation," *Cir Res* 99:1385-1394 (1999), which are hereby incorporated by reference in their entirety). The development of APD alternans requires that the slope of the restitution relation exceed 1, whereas if the slope of the restitution is less than 1, alternans will not occur.

The slope of the restitution relation, and the corresponding presence or absence of APD alternans, has been linked to spiral wave stability. If the slope of the APD restitution relation is <1, a spiral wave tends to stabilize and produce a periodic rhythm, the manifestation of which might be monomorphic ventricular tachycardia. If, however, the slope of the APD restitution relation is $\geq 1$, a single spiral wave may disintegrate into many spiral waves, manifest as VF. These transitions are illustrated in FIG. 3, using results generated by a computer model. Once initiated, a single stable spiral wave can be destabilized by increasing the slope of the restitution relation from <1 to $\geq 1$. Similarly, multiple wavelets can be induced to coalesce into a single spiral wave by reducing the slope of the restitution relation from $\geq 1$ to <1. Thus, a reduction of the slope of the restitution relation from $\geq 1$ to <1 is expected to prevent the induction of VF and to convert existing VF into a periodic rhythm.

Several recent studies have provided experimental and theoretical support for a causal relationship between APD restitution and VF (Garfinkel et al., "Preventing Ventricular Fibrillation by Flattening Cardiac Restitution," *Proc Natl Acad Sci USA* 97:6061-6066 (2000); Riccio et al., "Electrical Restitution and Spatiotemporal Organization During Ventricular Fibrillation," *Circ Res* 84:955-963 (1999); Koller et al., "Dynamic Restitution of Action Potential Duration During Electrical Alternans and Ventricular Fibrillation," *Am J Physiol* 275:H1635-H1642 (1998); Koller et al., "Effects of $[K+]_o$ on Electrical Restitution and Activation Dynamics During Ventricular Fibrillation," *Am J Physiol Heart Circ Physiol* 279:H2665-H2672 (2000); Fox et al., "Spatiotemporal Transition to Conduction Block in Canine Ventricle," *Circ Res.* 90:289-296 (2002); Chen et al., "Spirals, Chaos, and New Mechanisms of Wave Propagation," *Pacing Clin Electrophysiol (PAC)* 20:414-421 (1997); and Panfilov, A., "Spiral Breakup as a Model of Ventricular Fibrillation," *Chaos* 8:57-64 (1998), which are hereby incorporated by reference in their entirety. If the APD restitution relation contains a region of slope 1, APD alternans and VF are induced by pacing at short cycle lengths. If the slope of the APD restitution relation is reduced to less than one, APD alternans is suppressed and VF is not induced. Furthermore, if a fibrillating ventricle is exposed to a drug that reduces the slope of the restitution to less than 1, VF is converted to a periodic rhythm sustained by a single stable spiral wave (Garfinkel et al., "Preventing Ventricular Fibrillation by Flattening Cardiac Restitution," *Proc Natl Acad Sci USA* 97:6061-6066 (2000); Riccio et al., "Electrical Restitution and Spatiotemporal Organization During Ventricular Fibrillation," *Circ Res* 84:955-963 (1999); and Koller et al., "Effects of $[K+]_o$ on Electrical Restitution and Activation Dynamics During Ventricular Fibrillation," *Am J Physiol Heart Circ Physiol* 279:H2665-H2672 (2000), which are hereby incorporated by reference in their entirety).

Unfortunately, interventions that suppress VF experimentally (verapamil (Riccio et al., "Electrical Restitution and Spatiotemporal Organization During Ventricular Fibrillation," *Circ Res* 84:955-963 (1999), which is hereby incorporated by reference in its entirety), bretylium (Garfinkel et al., "Preventing Ventricular Fibrillation by Flattening Cardiac Restitution," *Proc Natl Acad Sci USA* 97:6061-6066 (2000), which is hereby incorporated by reference in its entirety) and hyperkalemia (Koller et al., "Effects of $[K+]_o$ on Electrical Restitution and Activation Dynamics During Ventricular Fibrillation," *Am J Physiol Heart Circ Physiol* 279:H2665-H2672 (2000), which is hereby incorporated by reference in its entirety) have unwanted actions that severely limit their clinical utility. Nevertheless, the effects of these interventions on restitution and VF have provided valuable insights regarding new, potentially more clinically relevant, drug targets. In particular, attempts to understand the mechanism by which calcium channel blockers alter APD restitution have led to the realization that increasing selected outward repolarizing currents also may flatten restitution, as presented in the examples.

The physiological mechanism associated with the initiation of ventricular fibrillation are broadly debated. The present invention affords the ability to characterize and identify the events initiating ventricular fibrillation. As demonstrated by the examples, the present invention also affords novel methods of identifying candidates for the treatment and prevention of ventricular fibrillation.

BRIEF DESCRIPTION OF THE DRAWINGS

FIGS. 2A-C show the restitution of action potential duration (APD). FIG. 2A shows the definition of APD, diastolic interval (DI), and cycle length (CL). The duration of the n+1th action potential ($APD_{n+1}$) is a function of the preceding DI ($D_{in}$). FIG. 2B shows the plot of APD versus preceding DI. FIG. 2C shows the plot of APD versus CL. Crosses are APDs during the CLs in which no alternans occurs. During APD alternans, unfilled circles are APDs during the long action potential, and filled circles are APDs during the short action potential. Modified, with permission, from Koller et al. (Koller et al., "Dynamic Restitution of Action Potential Duration During Electrical Alternans and Ventricular Fibrillation," *Am J Physiol* 275:H1635-H1642 (1998), which is hereby incorporated by reference in its entirety).

FIG. 3B).

FIG. 8A shows V restitution for four cases: $\beta$=17.408 (y-axis—second line from top; wild type), $\beta$=7.704 (y-axis—third line from top; V($I_{min}$)=50% of $V_{max}$), $\beta$=2.2028 (y-axis—fourth line from top; V($I_{min}$)=25% of $V_{max}$), and $\beta$=30.236 (y-axis—first line from top; V($I_{min}$)=90% of $V_{max}$). FIG. 8B shows a histogram for V($I_{min}$)=50% of $V_{max}$. Total counts=8879 (cf 67 205 for wild type). FIG. 8C shows a histogram for V($I_{min}$)=90% of $V_{max}$. Total counts=86 032. There were no counts for V($I_{min}$)=25% of $V_{max}$.

FIG. 9A shows steady-state D restitution for four cases: $\tau_D$=28 (y-axis—third line from top; wild type; max. slope=1.09), $\tau_D$=32 (y-axis—second line from top; max. slope=0.97), $\tau_D$=40 (y-axis—first line from top; max. slope=0.82) and $\tau_D$=20 (y-axis—fourth line from top; max. slope=1.45). FIG. 9B shows a histogram for $\tau_D$=32. Total counts=39 688. FIG. 9C shows a histogram for $\tau_D$=40. Total counts=21 185. FIG. 9D shows a histogram for $\tau_D$=20. Total counts=364 301.

FIG. 10A shows the steady-state D restitution for four cases: $\alpha$=0.2 (y-axis—second line from top; wild type; max. slope=1.09), $\alpha$=0.58 (y-axis—third line from top; max. slope=1.62), $\alpha$=0.08 (y-axis—fourth line from top; max. slope=2.65) and $\alpha$=0.1 (y-axis—first line from top; max. slope=1.09). FIG. 10B shows a histogram for $\alpha$=0.58. Total counts=48 387. FIG. 10C shows a histogram for $\alpha$=0.8. Total counts=43 715. FIG. 10D shows a histogram for $\alpha$=0.1. Total counts=87 433.

FIG. 14A shows an example of the reduction in the slope of the APD restitution relation after exposure to verapamil. FIG. 14B shows the corresponding reduction in the magnitude of APD alternans (AM) during pacing at different basic cycle lengths (BCL) after exposure to verapamil. FIG. 14C shows the effects of verapamil on the composite Fast Fourier Transform (FFT) of monophasic action potential (MAP) recordings during VF in arterially perfused canine ventricle. Verapamil, added after 35 min of VF had elapsed, converted the broad FFT spectra during VF to a single frequency. Modified, with permission, from Riccio et al. (Riccio et al., "Electrical Restitution and Spatiotemporal Organization During Ventricular Fibrillation," *Circ Res* 84:955-963 (1999), which is hereby incorporated by reference in its entirety).

DETAILED DESCRIPTION OF THE INVENTION

The present invention relates to a method of evaluating the effect of a physiological condition on the occurrence of ventricular fibrillation. This method involves providing a test system and initiating a ventricular fibrillation inducing sequence in the test system by interrupting normal sinus heart rhythm with premature electrical stimuli. Following the initiation of ventricular fibrillation a ventricular recovery sequence is initiated. The test system is subjected to a physiological condition before, during, and after initiating the ventricular fibrillation recovery sequence and the physiological conditions which affect ventricular fibrillation recovery are identified.

In carrying out this aspect of the present invention, the physiological condition to be tested can be velocity restitution, action potential duration restitution, or cardiac memory.

The step of initiating a ventricular fibrillation inducing sequence is carried out by: (1) initiating 4 premature stimuli under conditions effective to initiate an excitatory wave; (2) altering velocity recovery function to slow conduction at shorter rest intervals; (3) altering action potential duration recovery function to reduce sensitivity of action potential duration to a preceding rest interval; or (4) is carried out by increasing cardiac memory. The test system can be a test animal, a tissue, a cell culture, or an in vitro system.

Another aspect of the present invention relates to a method of identifying treatment candidates as therapeutic strategies for the prevention of ventricular fibrillation. This method involves providing a test system and initiating a ventricular fibrillation inducing sequence in the test system by interrupting normal sinus heart rhythm with premature electrical stimuli before, during, and after administering the treatment candidate to the test system. Treatment candidates which prevent the initiation step from inducing ventricular fibrillation are identified as therapeutic strategies for prevention of ventricular fibrillation.

In carrying out this aspect of the present invention, the treatment candidate is a pharmaceutical compound, such as a calcium channel antagonist. Alternatively, the treatment candidate is one or more electrical impulses.

Figure 8A:
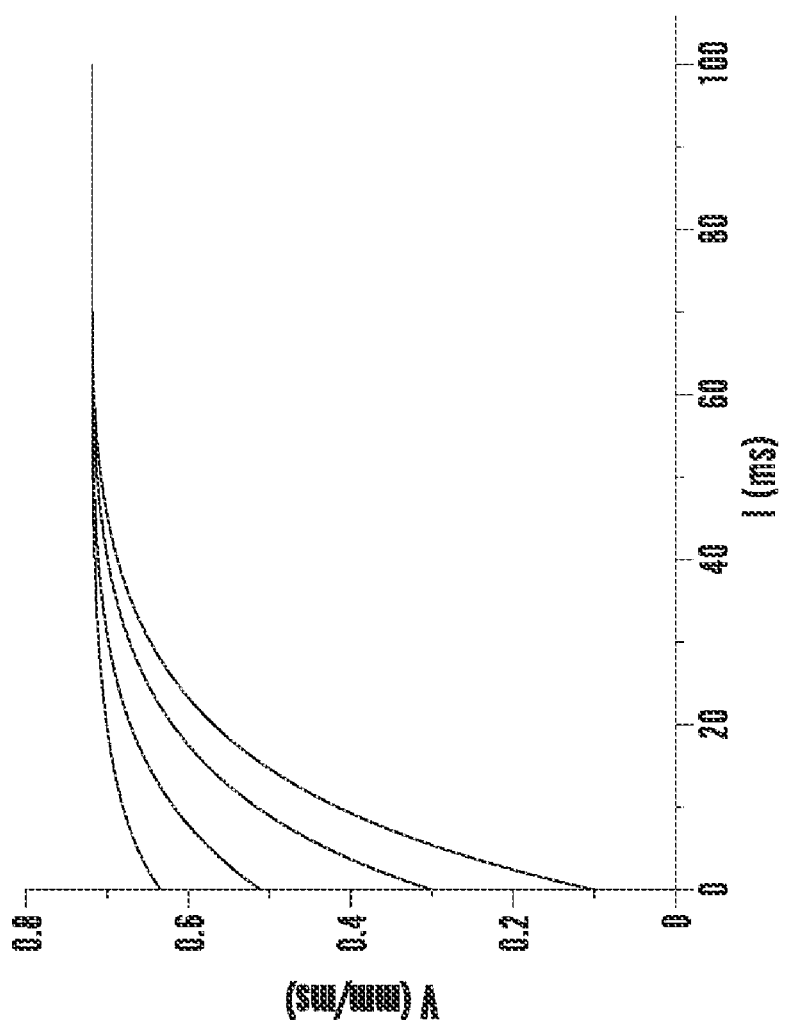
FIGS. 8A-C show the role of V restitution in type II block.
Figure 8B:
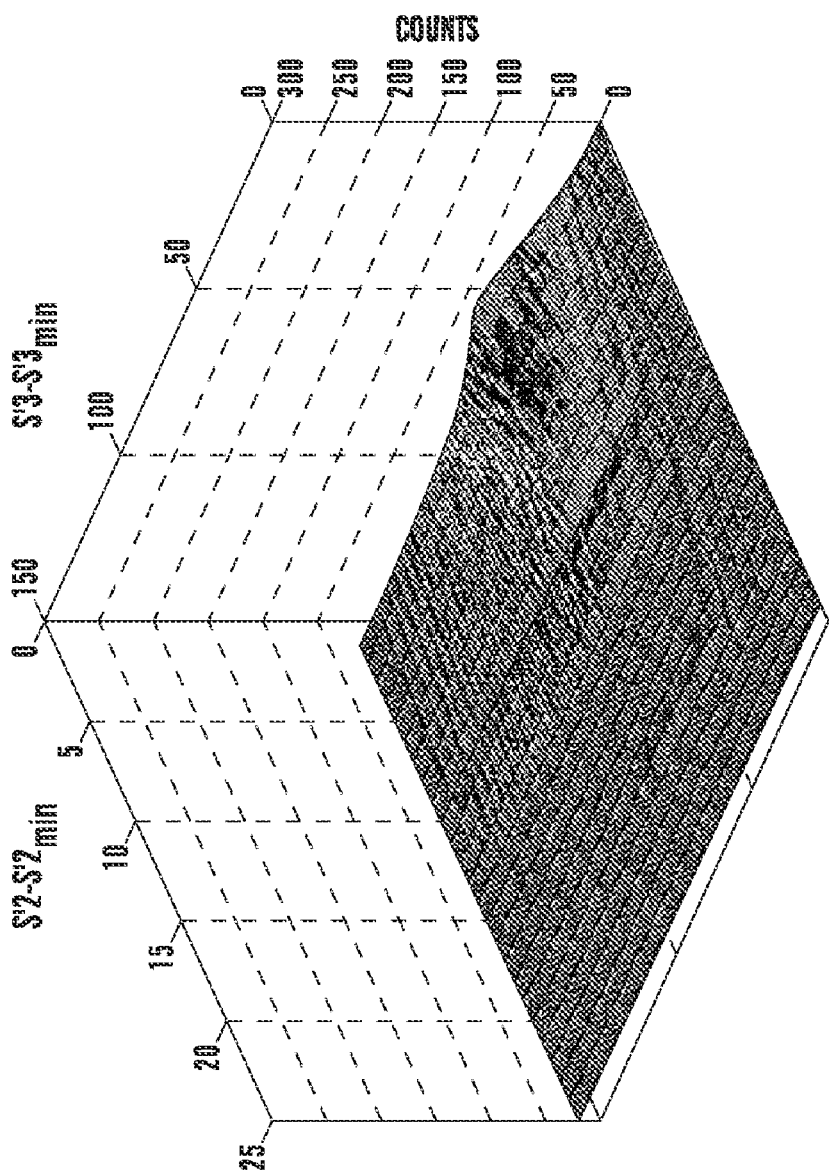
Figure 8C:
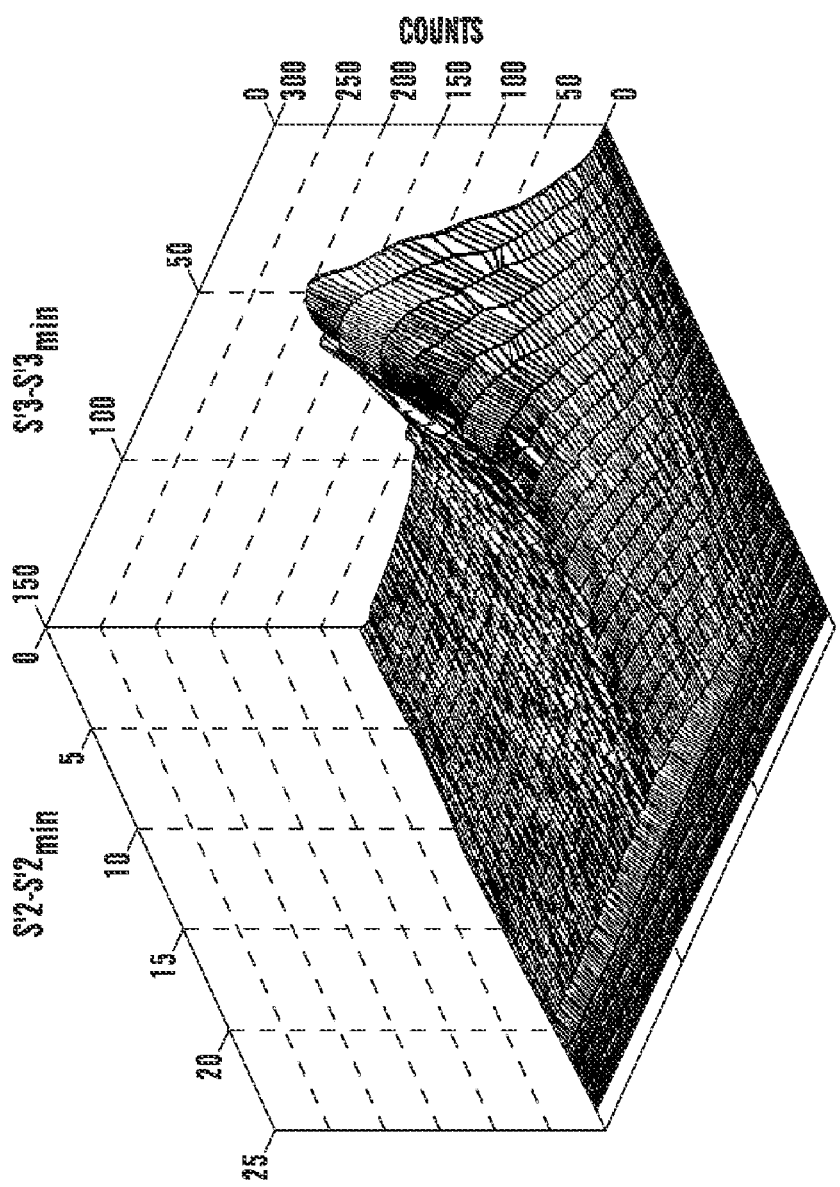

The step of identifying identifies treatment candidates which achieve velocity restitution values consistent with the histograms of FIGS. 8B and 8C as therapeutic strategies for prevention of ventricular fibrillation. Alternatively, the step of identifying identifies treatment candidates which achieve potential duration restitution values consistent with the histograms of FIGS. 8B and 8C as therapeutic strategies for prevention of ventricular fibrillation. Finally, the step of identifying identifies treatment candidates which achieve cardiac memory values consistent with the histograms of FIGS. 9B and 9C as therapeutic strategies for prevention of ventricular fibrillation.

Again, the test system can be a subject (i.e., a test animal or patient), a tissue, a cell culture, an in vitro system. The step of initiating a ventricular fibrillation inducing sequence can be carried out by initiating 4 premature stimuli under conditions effective to initiate an excitatory wave.

A further aspect of the present invention relates to a method of identifying treatment candidates as therapeutic strategies for treating ventricular fibrillation. This method includes providing a test system and initiating a ventricular fibrillation inducing sequence in the test system by interrupting normal sinus heart rhythm with premature electrical stimuli, resulting in ventricular fibrillation in the test system. Treatment candidates are administered to the test system undergoing ventricular fibrillation and treatment candidates which modulate ventricular fibrillation are identified as therapeutic strategies for treatment of ventricular fibrillation.

In carrying out this aspect of the present invention, the treatment candidate is a pharmaceutical compound, such as a calcium channel antagonist. Alternatively, the treatment candidate can be one or more electrical impulses.

The step of identifying identifies treatment candidates which achieve velocity restitution values consistent with the histograms of FIGS. 8B and 8C as therapeutic strategies for prevention of ventricular fibrillation. Alternatively, the step of identifying identifies treatment candidates which achieve potential duration restitution values consistent with the histograms of FIGS. 9B and 9C as therapeutic strategies for prevention of ventricular fibrillation. As yet another alternative, the step of identifying identifies treatment candidates which achieve cardiac memory values consistent with the histograms of FIGS. 10B and 10C as therapeutic strategies for prevention of ventricular fibrillation.

In carrying out this aspect of the present invention, the test system can be a subject (i.e. a test animal or patient), a tissue, a cell culture, or an in vitro system. The step of initiating a ventricular fibrillation inducing sequence is carried out by initiating 4 premature stimuli under conditions effective to initiate an excitatory wave.

The present invention also relates to a method of evaluating the predisposition of a subject for the induction of ventricular fibrillation from a condition of ventricular tachycardia. This method involves providing a subject in ventricular tachycardia and monitoring the electrical stimuli in the heart of the test animal. It is then determined if a sequence of rest interval values correspond to rest interval values predicted to lead to ventricular fibrillation consistent with the histogram of FIG. 7.

Figure 7:
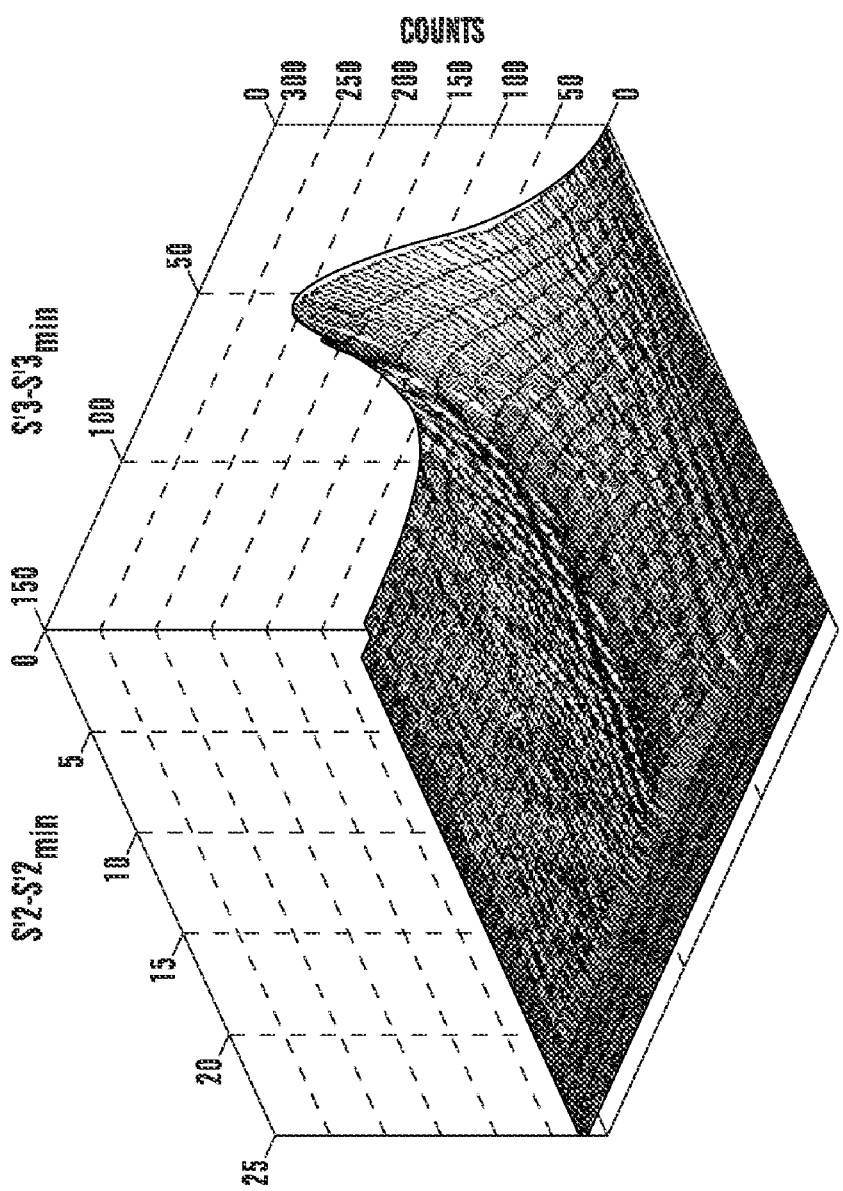
FIG. 7 shows a histogram of the incidence of type II conduction block in the wild type model. $\alpha$=0.2, $\tau_D$=28 and $\beta$=17.408. The height at each point in (S'2, S'3) space corresponds to the number of blocks found at beat S'3, S'4 or S'5 for a given (S'2, S'3) pair. Total counts=67 205. S'$2_{min}$ and S'$3_{min}$ are the minimum time intervals at points S'2 and S'3, respectively, that allow conduction down the fiber. $\tau_D$ is the time interval between activations used to adjust dependence of the D recovery function on I. $\beta$ is the velocity variable which was varied to adjust the value of V at I=$I_{min}$. $\alpha$ is the memory variable (which varied between zero and unity) which was used to determine the influence of memory on D.
Figure 17:
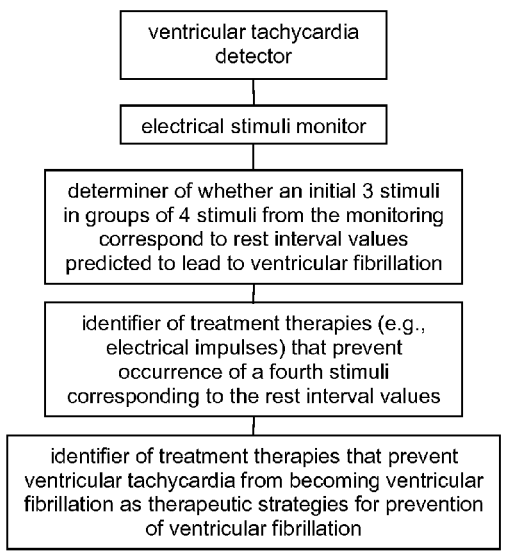
FIG. 17 is a schematic diagram showing a system according to one embodiment of the present invention.

Another aspect of the present invention relates to a method of identifying treatment candidates as therapeutic strategies for preventing ventricular tachycardia from developing into ventricular fibrillation. (See FIG. 17). This involves providing a subject in ventricular tachycardia and monitoring the electrical stimuli in the heart of the test animal. It is then determined if the initial 3 stimuli in groups of 4 stimuli correspond to rest interval values predicted to lead to ventricular fibrillation consistent with the histogram of FIG. 7. Treatment candidates which prevent occurrence of a fourth stimuli corresponding to a rest interval value predicted to lead to ventricular fibrillation consistent with the histogram of FIG. 7 are identified. Treatment candidates which prevent ventricular tachycardia from becoming ventricular fibrillation are identified as therapeutic strategies for preventing ventricular fibrillation.

In carrying out this aspect of the present invention, the treatment candidate is a pharmaceutical compound, such as a calcium channel antagonist. Alternatively, the treatment candidate can be one or more electrical impulses.

In one embodiment of this aspect of the present invention, the identifying step identifies treatment candidates which achieve velocity restitution values consistent with the histograms of FIGS. 8B and 8C as therapeutic strategies for prevention of ventricular fibrillation. Alternatively, the step of identifying identifies treatment candidates which achieve potential duration restitution values consistent with the histograms of FIGS. 9B and 9C as therapeutic strategies for prevention of ventricular fibrillation. A further alternative is that the identifying step identifies treatment candidates which achieve cardiac memory values consistent with the histograms of FIGS. 10B and 10C as therapeutic strategies for prevention of ventricular fibrillation.

Previous theoretical and experimental studies of the impact of dynamic heterogeneity of repolarization on the development of conduction block were conducted in computer models of a homogenous 1-dimensional cable and in isolated Purkinje fibers during fixed pacing. As the pacing cycle length was shortened progressively, a transition from 1:1 phase locking to a concordant alternans (2:2 locking) to discordant alternans to intermittent 2:1 conduction block occurred (Fox et al, "Spatiotemporal Transition to Conduction Block in Canine Ventricle," *Circ Res.* 90:289-96 (2002), which is hereby incorporated by reference in its entirety). These results confirmed the predictions of previous computer modeling studies of these phenomena (Watanabe et al., "Mechanisms for Discordant Alternans,"*J Cardiovasc Electrophysiol* 12:196-206 (2001), which is hereby incorporated by reference in its entirety) and extended experimental observations that the development of discordant alternans was associated with local conduction block and the initiation of reentry (Pastore et al., "Mechanism Linking T-Wave Alternans to the Genesis of Cardiac Fibrillation," *Circulation* 99:1385-94 (1999); Pastore et al., "Role of Structural Barriers in the Mechanism of Alternans-Induced Reentry," *Circ Res.* 87:1157-63 (2000), which are hereby incorporated by reference in their entirety). In addition, they demonstrated that complex dynamics was possible in a homogenous 1-dimensional cable, in the absence of intrinsic heterogeneity or anisotropy, and that the mechanism for the dynamics could be described using simple unidimensional maps for the restitution of APD and CV.

Figure 1:
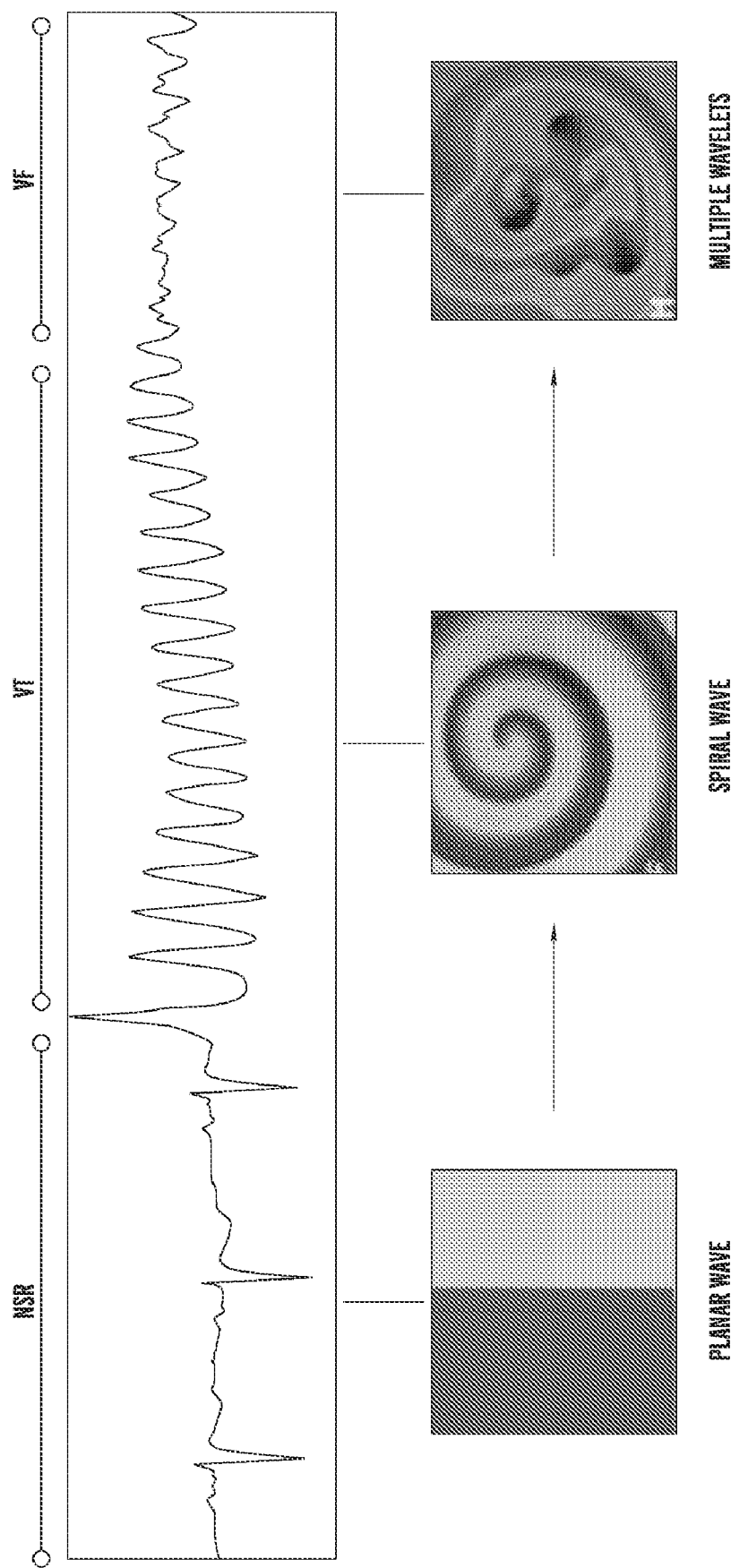
FIG. 1 shows the proposed evolution of cardiac wave propagation patterns underlying the transition from a normal cardiac rhythm to ventricular fibrillation. Transition from normal sinus rhythm (NSR) to ventricular tachycardia (VT) and ventricular fibrillation (VF), as recorded on the surface electrocardiogram are shown. Corresponding transitions from a planar wave to a single wave to multiple spiral waves are shown.
Figure 2A:
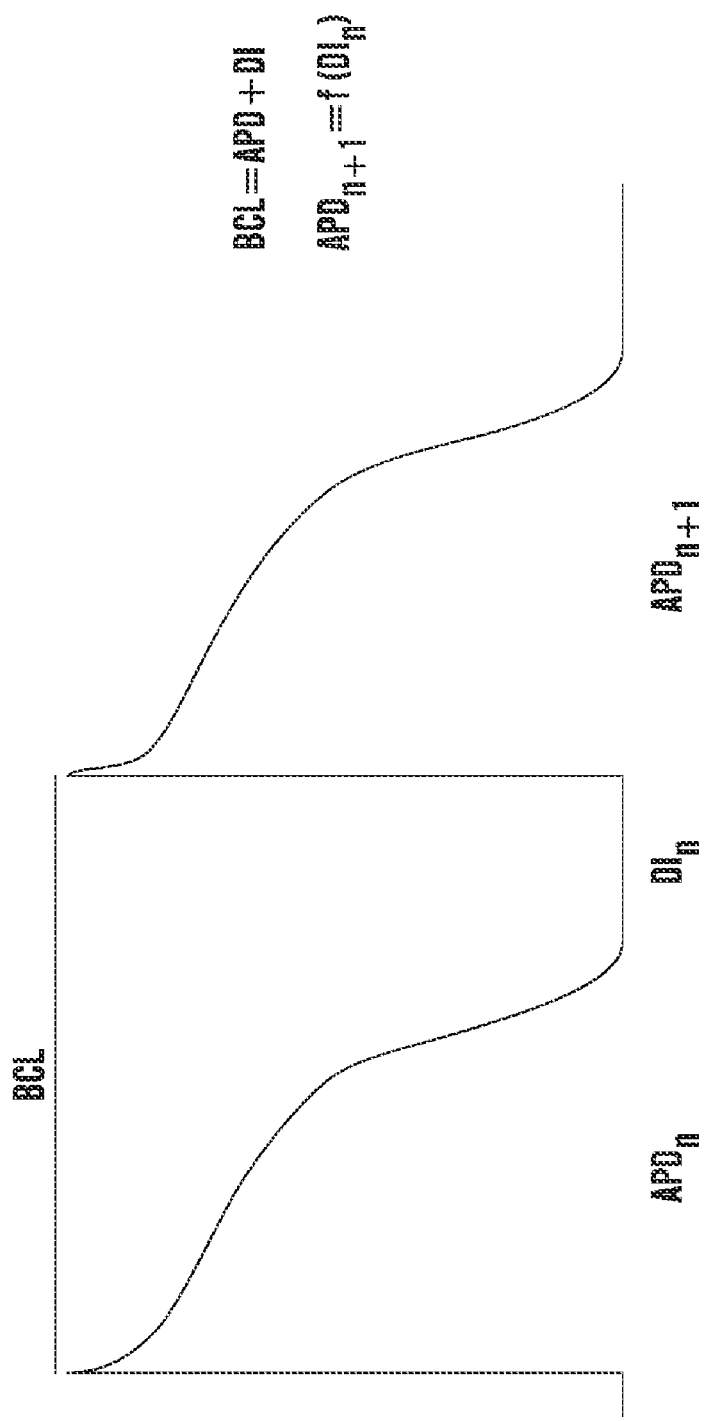
Figure 3B:
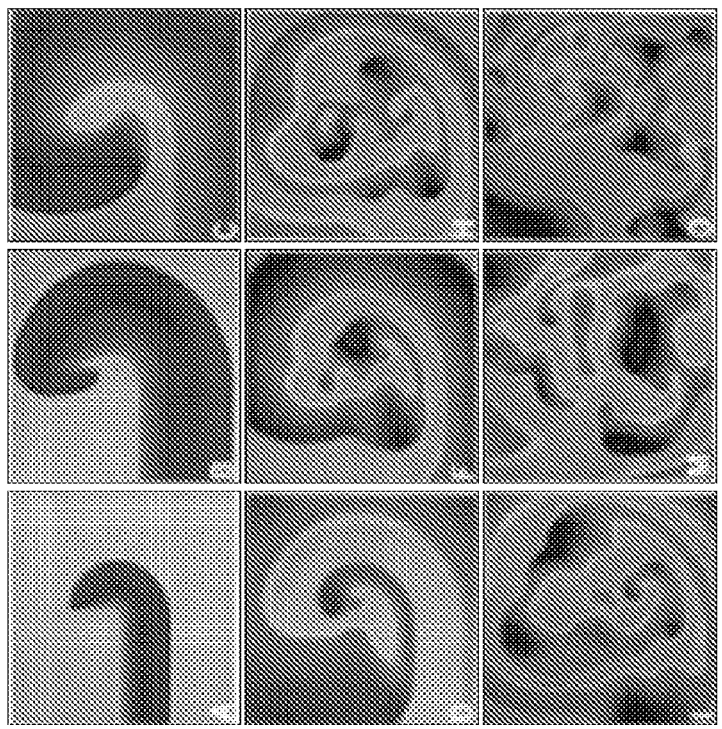
FIGS. 3A-B show the wave patterns in a computer model of cardiac activation. Sequential snapshots (A-1) of activation during the development of a stable single spiral wave under conditions in which the slope of the restitution relation for action potential duration is <1 (FIG. 3A). The transition form a single spiral wave into many spiral waves for a restitution slope >1 (A-O, with some intervening steps deleted.
Figure 3A:
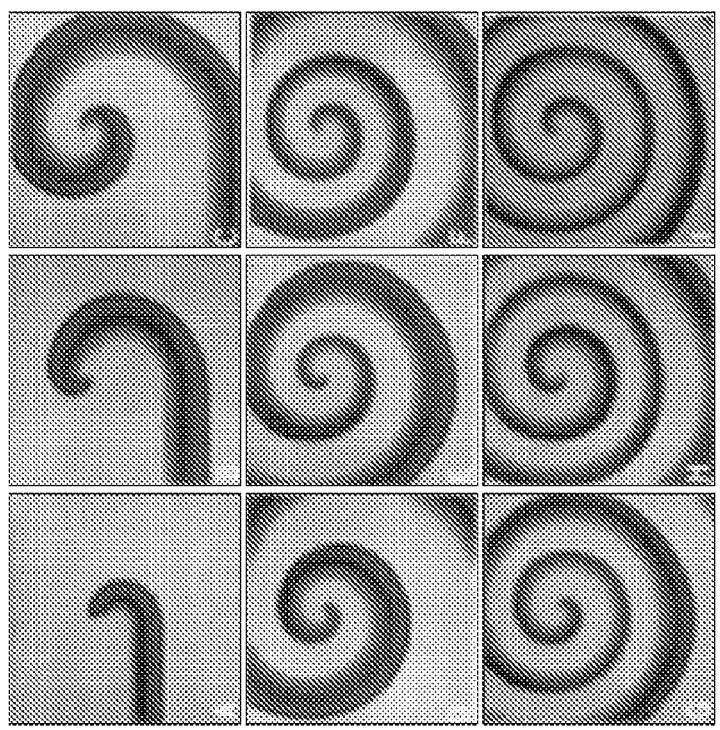
Figure 4A:
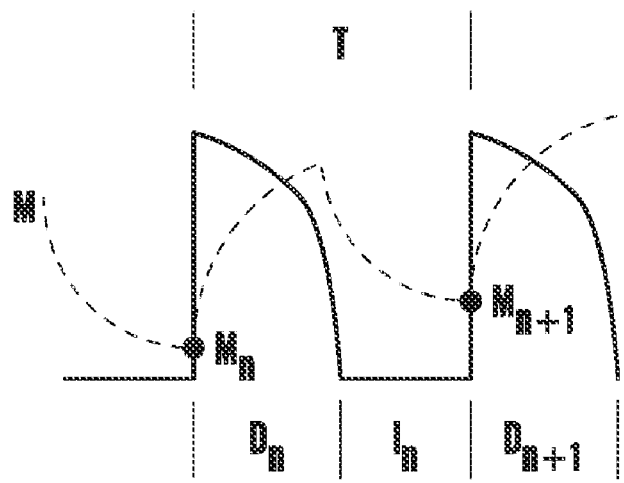
FIG. 4A shows a schematic representation of the relationships between stimulus period (T), action potential duration (D), diastolic interval (I) and memory (M).
Figure 4B:
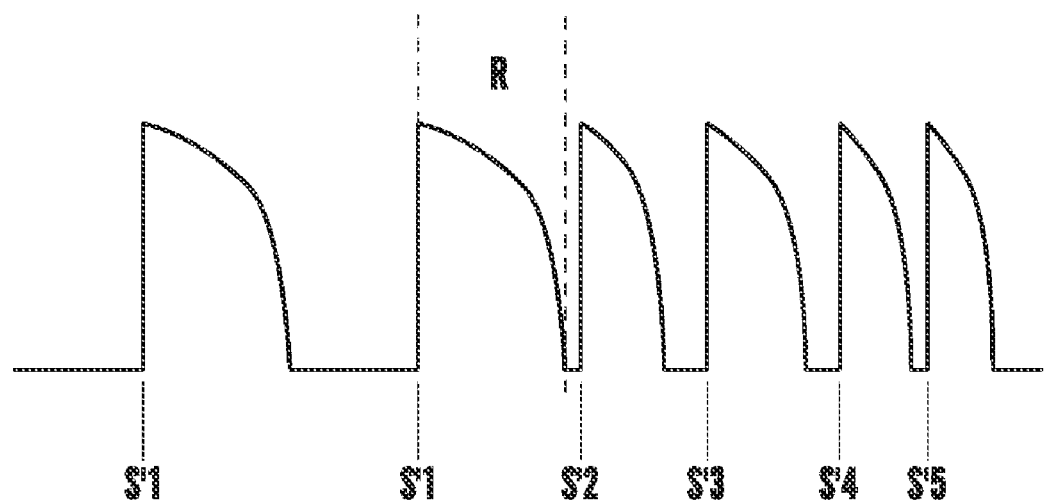
FIG. 4B shows an example of the stimulation protocol. The model fibre was paced for ten beats at a constant S'1-S'1 interval, after which a series of premature stimuli (S'2-S'5) was delivered. R indicates the refractory period of a cardiac cell, during which the delivery of a stimulus does not produce a propagated response.
Figure 5:
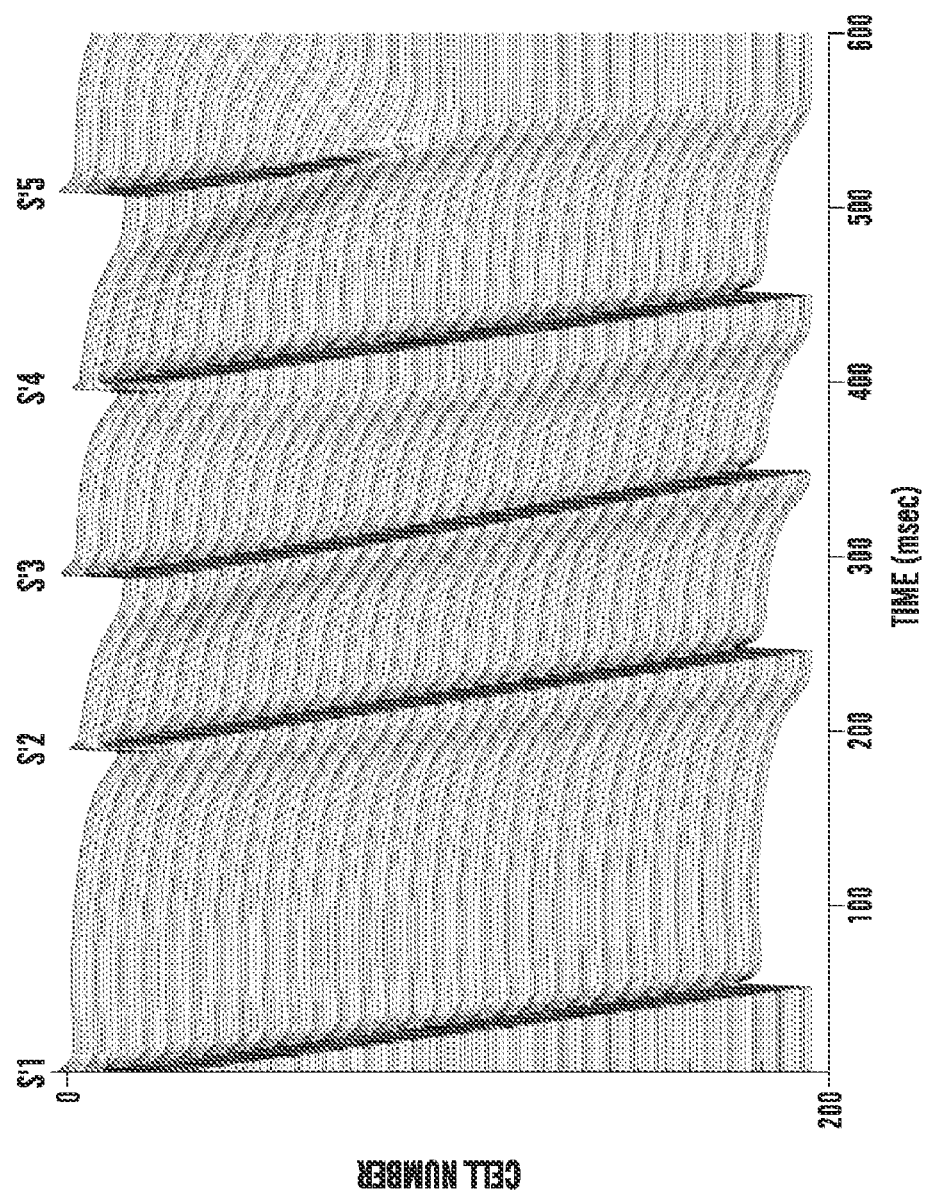
FIG. 5 shows the spatial dispersion of repolarization induced in an ionic model of a homogenous 1-dimensional cable by multiple premature stimuli. Note that short duration action potentials at the site of stimulation increase in duration as they propagate alone the fiber, whereas long duration action potentials shorten. The resultant discordant alternans pattern culminates in conduction block.

The evolution of dynamics during fixed pacing occurs relatively gradually, which allows this phenomenon to be studied in the quasi-steady-state. As a result, a detailed description of the dynamics and identification of the underlying mechanism is possible. It is unlikely, however, that prolonged activation at a short constant cycle length initiates VF in patients at risk for sudden death. Therefore, investigations into a scenario that is more common in such patients—initiation of VF following a run of non-sustained VT, were begun. In the present invention, computer models of a homogenous 1-dimensional cable were generated using a coupled maps memory model (Fox et al., "Period-Doubling Instability and Memory in Cardiac Tissue," *Phys Rev Lett* 89:138101 (2002), which is hereby incorporated by reference in its entirety) and an ionic model (Fox et al., "Ionic Mechanism of Electrical Alternans," *Am J Physiol Heart Circ Physiol* 282:H516-30 (2002), which is hereby incorporated by reference in its entirety). The models were paced at a cycle length of 1000 or 500 ms for 50 beats, after which a series of premature stimuli was delivered (FIGS. 4 and 5). Premature stimuli delivered at short DI (e.g., $S'_2$ in FIG. 5) elicited action potentials at the site of stimulation that, in accordance with the relevant APD and CV restitution relations were short in duration and conducted slowly. Slow conduction along the fiber provided progressively more recovery time as the action potential conducted down the fiber. Accordingly, DI increased along the fiber, as did the corresponding APD, resulting in a discordance between APD at the site of stimulation and at the distal end of the fiber. Conversely, premature stimuli delivered at longer DI ($S'_3$ in FIG. 5) produced longer duration action potentials that conducted more rapidly. The more rapidly conducting action potentials impinged progressively on the preceding DI as they conducted along the fiber, creating a shorter DI and corresponding APD. Once again, discordant APD between the site of stimulation and the distal end of the fiber resulted. The spatial dispersion of repolarization caused by this sequence of cycle lengths could be amplified by the delivery of multiple premature stimuli, eventually resulting in conduction block ($S'5$ in FIG. 5).

To more completely characterize this sequence of events, all possible combinations of $S'_2$—$S'_5$ that produced conduction block in the coupled maps model (block also occurred with many fewer combinations of $S'_2$—$S'_3$ and many more combinations of $S'_2$—$S'_7$) were determined. Although approximately 67,000 combinations produced conduction block, the distribution of such combinations was not random, but was clustered according to specific $S'_2$ and $S'_3$ intervals, as shown in FIG. 7. The incidence of block was greatest when $S'_2$ was delivered at a coupling interval near $S'_1S'_{2min}$ (the shortest $S'_1S'_2$ interval that produced a propagated response) and $S'_3$ was delivered at a coupling interval approximately 50 ms longer than $S'_2S'_{3min}$. Although not shown on this 3-dimensional plot, the $S'_3S'_4$ interval most often associated with block was near $S'_3S'_{4min}$, whereas the $S'_4S'_5$ interval was approximately 10 ms longer than $S'_4S'_{5min}$. This short-long-short-intermediate pattern of stimulation produced discordant alternans and conduction produced discordant alternans and conduction block of the type shown in FIG. 5. Also determined was the impact of changes in the slope of the APD restitution relation, the magnitude of memory, the shape of the CV restitution relation and the strength of cell coupling. In general, the incidence of conduction block was reduced by decreasing the slope of the APD restitution relation, increasing memory, increasing cell coupling and extending the CV restitution relation to permit slow conduction (thereby preventing "head-tail" interactions) (Fox et al., Dynamic Mechanism for Conduction Block in Heart Tissue," *New J Phys.* 5:101.1-101.14 (2003), which is hereby incorporated by reference in its entirety).

EXAMPLES

The following examples are provided to illustrate embodiments of the present invention but are by no means intended to limit its scope.

Example 1

Methods of Examining the Dynamic Mechanism for Conduction Block in Heart Tissue

The mechanism for conduction block following the delivery of multiple premature stimuli using a one-dimensional computer model of a canine heart fiber is presented. The fiber was stimulated at one end at a cycle length near normal canine sinus rhythm ($S'1=500$ ms). After ten beats at $S'1$, four premature stimuli were delivered ($S'2$, $S'3$, $S'4$ and $S'5$). The coupling intervals between these premature intervals were varied and conduction of the resultant action potentials was observed (FIG. 4). For each combination of premature stimuli, one of three possible outcomes occurred: 1) the stimulus elicited an action potential that propagated down the entire fiber; 2) the stimulus did not produce an action potential (Type I block); 3) the stimulus elicited an action potential that blocked before reaching the end of the fiber (Type II block).

The first two cases would not be conducive to the development of wave break and initiation of reentry, in that conduction of the premature response either does not occur at all or occurs equally well everywhere along the fiber. The third case, however, could lead to wave break and spiral wave initiation if it occurred in two- and three-dimensional tissue, provided the block was local. The development of local block would be facilitated in intact myocardium by twist anisotropy and intrinsic heterogeneity.

To assess the vulnerability of the simulated tissue to Type II block, the S'2-S'3-S'4-S'5 combinations were applied in the following way: the S' 1-S'2 interval was varied from the minimum value that conducted (S'1-S'2$_{min}$) to S'1-S'2$_{min}$+20 ms. For each S'1-S'2 interval, the S'2-S'3 interval and the S'3-S'4 interval were varied in combination from the minimum value that conducted up to a value of 250 ms for each interval. Finally, for each S'2-S'3-S'4 combination that conducted, the S'4-S'5 interval was varied from the minimum that generated an action potential at the site of stimulation to the minimum value that conducted down the entire fiber. If no S'2-S'3-S'4-S'5 combination was found that produced conduction block for more than a 20 ms window in either the S'2-S'3 interval or the S'3-S'4 interval, the search was halted for that interval. All intervals were varied in steps of 1 ms.

Example 2

Coupled Maps Model

One aspect of the present invention is conducted using a coupled maps model of a one-dimensional cardiac fiber that has been described in detail elsewhere (Fox et al., "Period-Doubling Instability and Memory in Cardiac Tissue," *Phys Rev Lett* 89:138101 (2002) and Fox et al, "Spatiotemporal Transition to Conduction Block in Canine Ventricle," *Circ Res*. 90:289-96 (2002), which are hereby incorporated by reference in their entirety). Briefly, the model is based on the equation $$I_{n+1}(x_i) = T_{n+1}(x_i) - D_{n+1}(x_i) \quad (1)$$

$T_{n+1}(x_i)$ was the time interval between activations of site $x_i$. It was determined by including the time delays caused by the propagation from the pacing site to site $x_i$, which yielded $$T_{n+1}(x_i) = \tau + \sum_{j=0}^{i-1} \frac{\Delta x}{V_{n+1}(x_j)} - \sum_{j=0}^{i-1} \frac{\Delta x}{V_n(x_j)}. \quad (2)$$

$\tau$ was the time interval between activations applied to the pacing site and $\Delta x=0.1$ was the length of a single cell (time units in ms and space units in mm). The conduction velocity $V_n(x_i)$ depended only on I through the velocity recovery function $V_n=c(I_n)$ given by $c(I)=V_{max}(1-\exp(-(I+\beta)/\delta))$. $V_{max}=0.72$, $\delta=14$, and $\beta$ was varied to adjust the value of V at $I=I_{min}$. D was determined locally based on a memory model mapping (8) given by:

$$M_{n+1} = g(M_n, I_n, D_n) = e^{-I_n/\tau_m}[1 + (M_n - 1)e^{-D_n/\tau_m}] \quad (3)$$

$$D_{n+1} = f(M_{n+1}, I_n) = (1 - \alpha M_{n+1})\left(A + \frac{B}{1 + e^{-(I_n-C)/\tau_D}}\right).$$

$\tau_m$ was the time constant of accumulation and dissipation of memory (both constants were chosen to be the same). A=88, B=122, C=40, and $\tau_m$=180 (Fox et al., "Period-Doubling Instability and Memory in Cardiac Tissue," *Phys Rev Lett* 89:138101 (2002), which is hereby incorporated by reference in its entirety). $\alpha$ and $\tau_D$ were varied in this study. $\alpha$ (which varied between 0 and 1) determined the influence of memory on D, and $\tau_D$ was used to adjust the dependence of the D recovery function on I (Fox et al., "Period-Doubling Instability and Memory in Cardiac Tissue," *Phys Rev Lett* 89:138101 (2002), which is hereby incorporated by reference in its entirety).

Coupling between sites was included by using the diffusion terms from Echebarria and Karma (Echebarria et al., "Instability and Spatiotemporal Dynamics of Alternans in Paced Cardiac Tissue," *Phys Rev Lett* 88:208101 (2002), which is hereby incorporated by reference in its entirety). These terms modeled the electronic current that flowed out of (into) a cell and into (out of) its neighbor if the action potential of the first cell was longer (shorter) than that of its neighbor. Including diffusion then yielded $$D_{n+1} = f(M_{n+1}, I_n) + \xi^2 \nabla^2 D_{n+1} - w \nabla D_{n+1}, \quad (4)$$

with $\xi=1.0$ and $w=0.35$. Discretizing the derivatives produced a tri-diagonal linear system of equations that could then be solved easily. The defining equation for the model was therefore $$M_{n+1} = g(M_n, I_n, D_n) \quad (5)$$

$$D_{n+1} = f(M_{n+1}, I_n) + \xi^2 \nabla^2 D_{n+1} - w \nabla D_{n+1}$$

$$I_{n+1}(x_i) = \tau + \sum_{j=0}^{i-1} \frac{\Delta x}{c(I_{n+1}(x_j))} - \sum_{j=0}^{i-1} \frac{\Delta x}{c(I_n(x_j))} - D_{n+1}(x_i)$$

Finally, conduction block was modeled by setting $f=0$ for $I<I_{min}=2$.

Example 3

Characterization of Type II Conduction Block in Wild-Type Model

Figure 6:
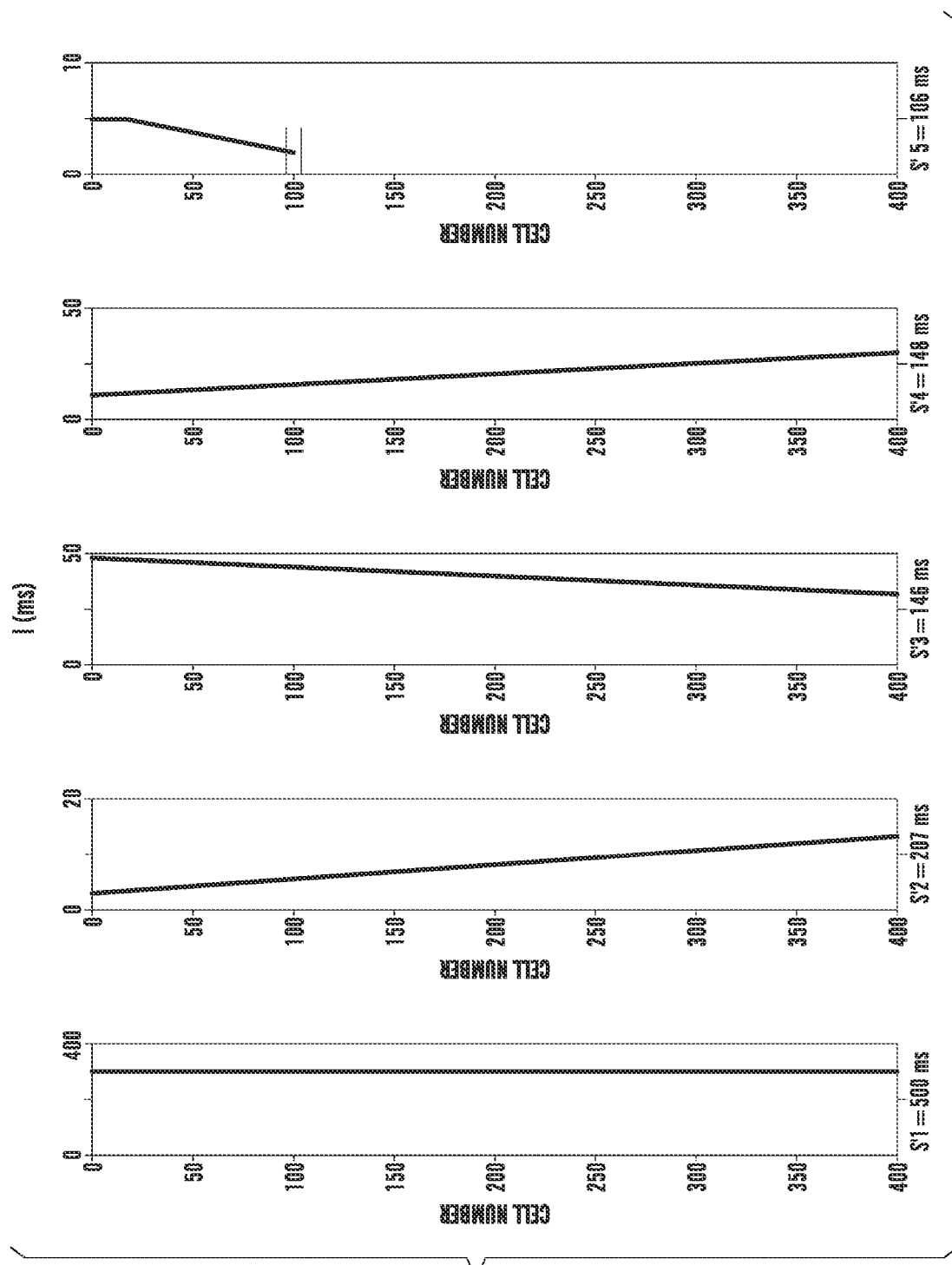
FIG. 6 shows an example of a type II conduction block in the coupled maps model. Each panel shows I as a function of cell number for the last S'=500 ms beat (left panel) and for beats S'2=207 ms, S'3=146 ms, S'4=148 ms and S'5=106 ms. Note the difference in scale for each beat. Conduction block, corresponding to I<$I_{min}$, occurs near cell 100 on the S'5 beat and is denoted by two horizontal black lines.

FIG. 6 shows a typical example of type II conduction block in the baseline model (hereafter called the wild type model). Despite the homogeneous state that existed at the end of the S'1 stimuli, dynamical heterogeneity developed following delivery of S'2, secondary to V restitution. Heterogeneity was manifest as a short-to-long gradient in I, which was magnified by subsequent premature stimuli until the action potential generated by the S'5 stimulus encountered a region where $I<I_{min}$ and conduction failed.

FIG. 7 shows a histogram of type II conduction block at various S'2 and S'3 intervals generated from the wild type model. Note the presence of a large peak centered at an S'2 very close to the minimum value for conduction and at an S'3 approximately 50 ms longer than the minimum value for conduction. Surrounding the peak is a flat plateau region of five to ten blocks per bin that extends throughout the entire (S'2, S'3) region that was explored numerically. An overwhelming majority of these instances of block occurred after the S'5 stimulus. However, six examples of 'early block' were found after an S'4 stimulus, and one was found after an S'3 stimulus. The latter explain the presence of the plateau in the histogram; the plateau is made up of 'degenerate' counts in which long S'2 or S'3 intervals that maintained the initial S'1 homogeneity were followed by early block intervals leading to block at S'5.

Since conduction block occurs when $I<I_{min}$, changes in $I_{min}$ will produce significant changes in the incidence of conduction block. Because $I_{min}$ is a component of the functions that control V restitution, D restitution and M, changes in $I_{min}$ influence all three dynamic variables. $I_{min}$ was fixed and individually the roles that V restitution, D restitution and M played in determining the risk of type II block, as assessed by the S'2-S'3-S'4-S'5 protocol, was examined.

Example 4

Contribution of V Restitution to Conduction Block

V restitution played two important roles in the development of conduction block. First, as mentioned above, V restitution was the source of the initial heterogeneity after delivery of the S'2 stimulus. The S'2 stimulus was delivered just after the refractory period of the last S'1 beat so that I at the site of stimulation was short (see FIG. 4). The short I produced slow V, which increased I for cells distal to the stimulus site. This initial dispersion in I following S'2 was magnified by steep D restitution at each subsequent beat, ultimately leading to conduction block several beats later.

Second, the value of the V restitution curve at $I_{min}$ was an important parameter in determining the likelihood of conduction block, as illustrated by FIG. 8. FIG. 8A shows V restitution curves with four different values for the W.) (90, 75, 50, and 25% of $V_{max}$). $V(I_{min})$ in the wild type model was 75% of $V_{max}$. FIG. 8B shows a histogram for $V(I_{min})$=50% of $V_{max}$, and FIG. 8C shows the histogram for $V(I_{min})$=90% of $V_{max}$. For $V(I_{min})$=90% of $V_{max}$, the model had roughly 30% more instances of conduction block than in the wild type model, whereas the model with the lower cut-off values produced dramatically fewer instances of conduction block. In fact, the model with $V(I_{min})$=25% of $V_{max}$ produced no cases of type II block. This result did not depend on the steepness of the V restitution curve. For example, no cases of type II block were found for a model with $\beta$=−1.4 and $\delta$=2.0, which also had $V(I_{min})$=25% of $V_{max}$, but had a much steeper slope. The lack of type II block when $V(I_{min})$=25% of $V_{max}$ can be understood by noting that if the V restitution curve approaches zero at $I_{min}$, then a propagating wave that approaches a region with a very small I can slow down to allow I to increase just in front of it, permitting continued conduction.

Example 5

Contribution of D Restitution to Conduction Block

Figure 9A:
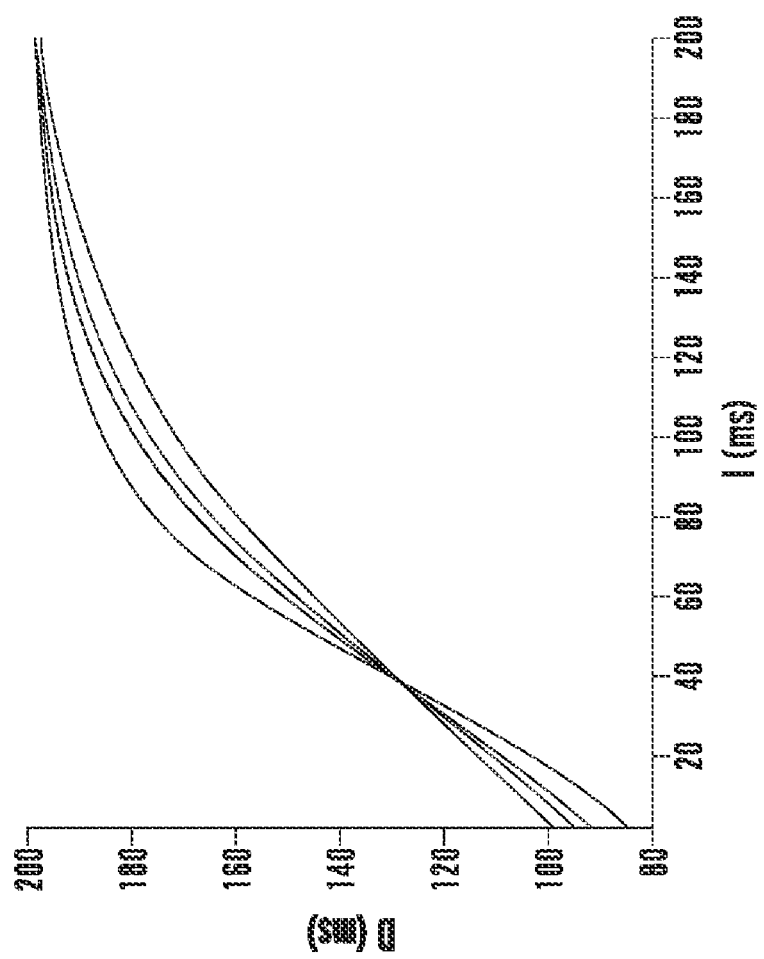
FIGS. 9A-D show the role of D restitution in type II block.
Figure 9B:
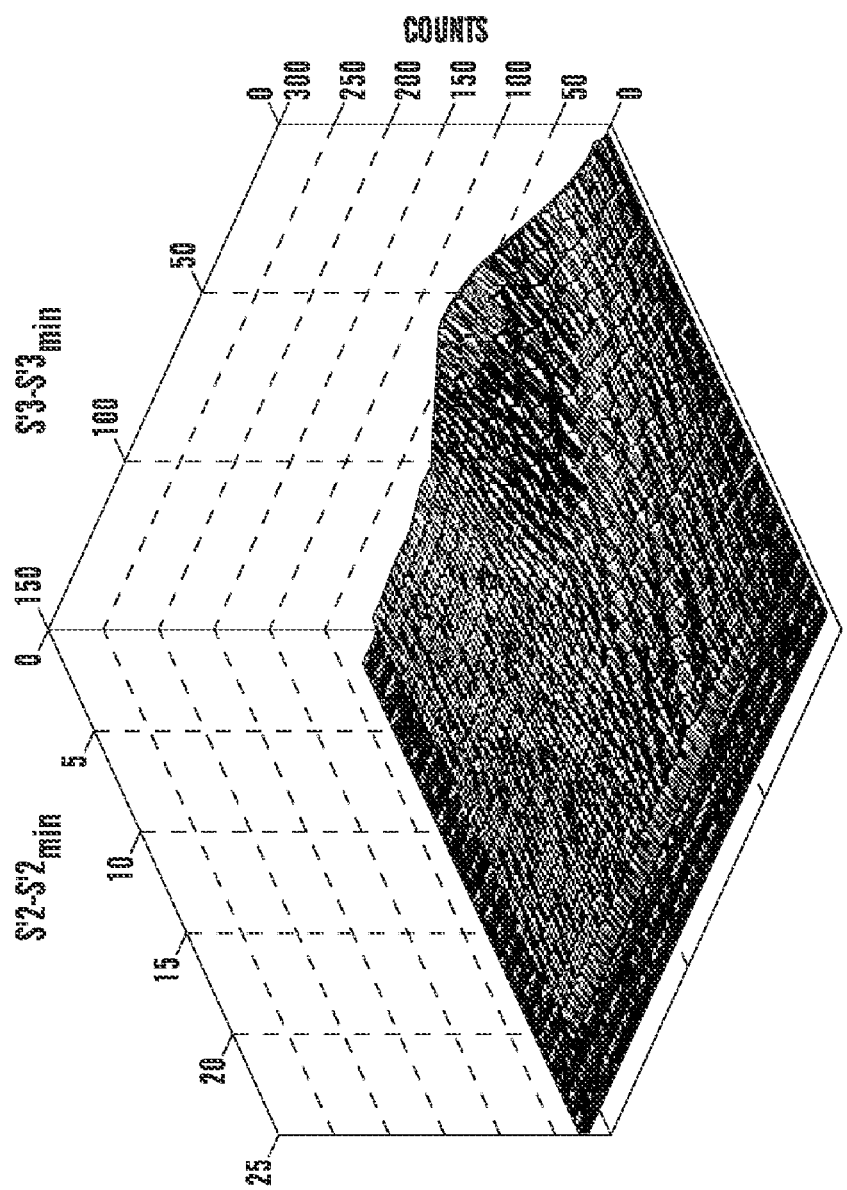
Figure 9C:
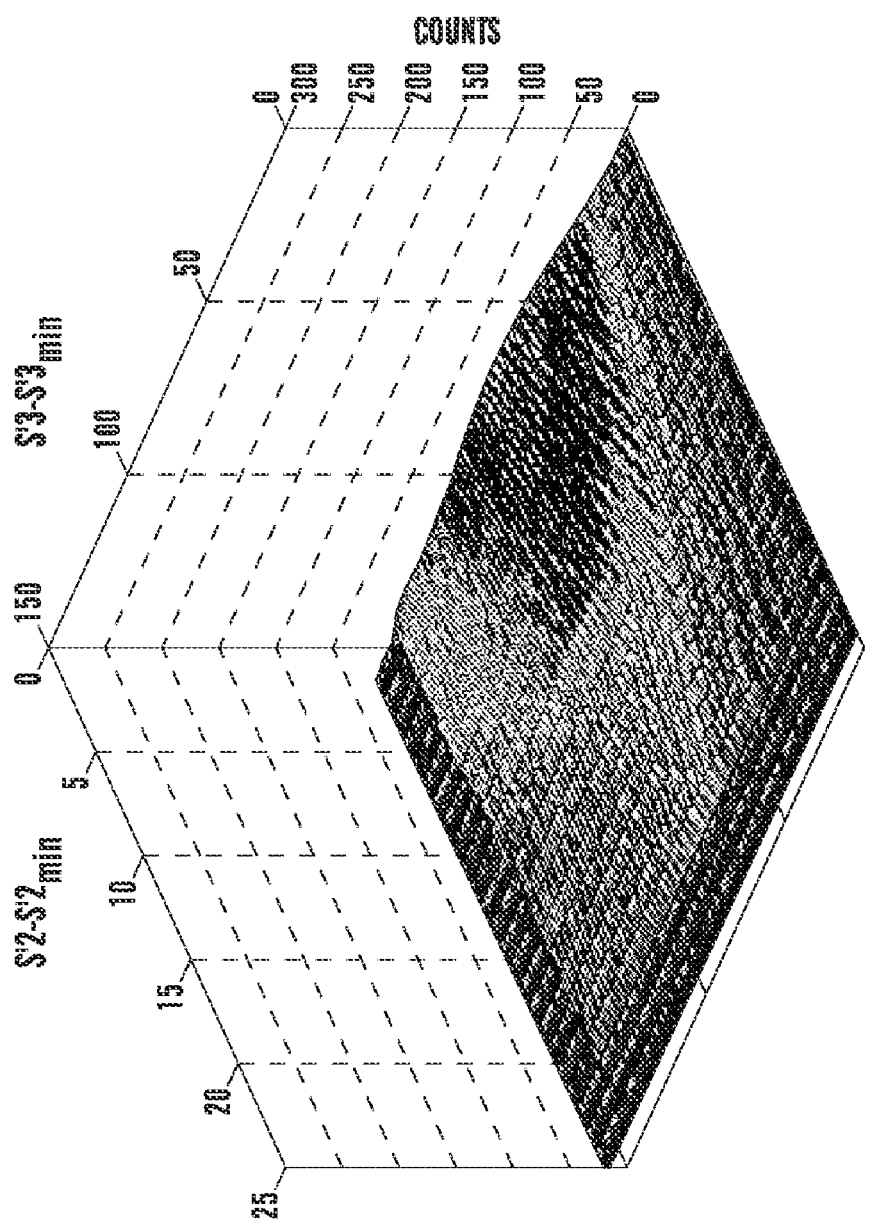
Figure 9D:
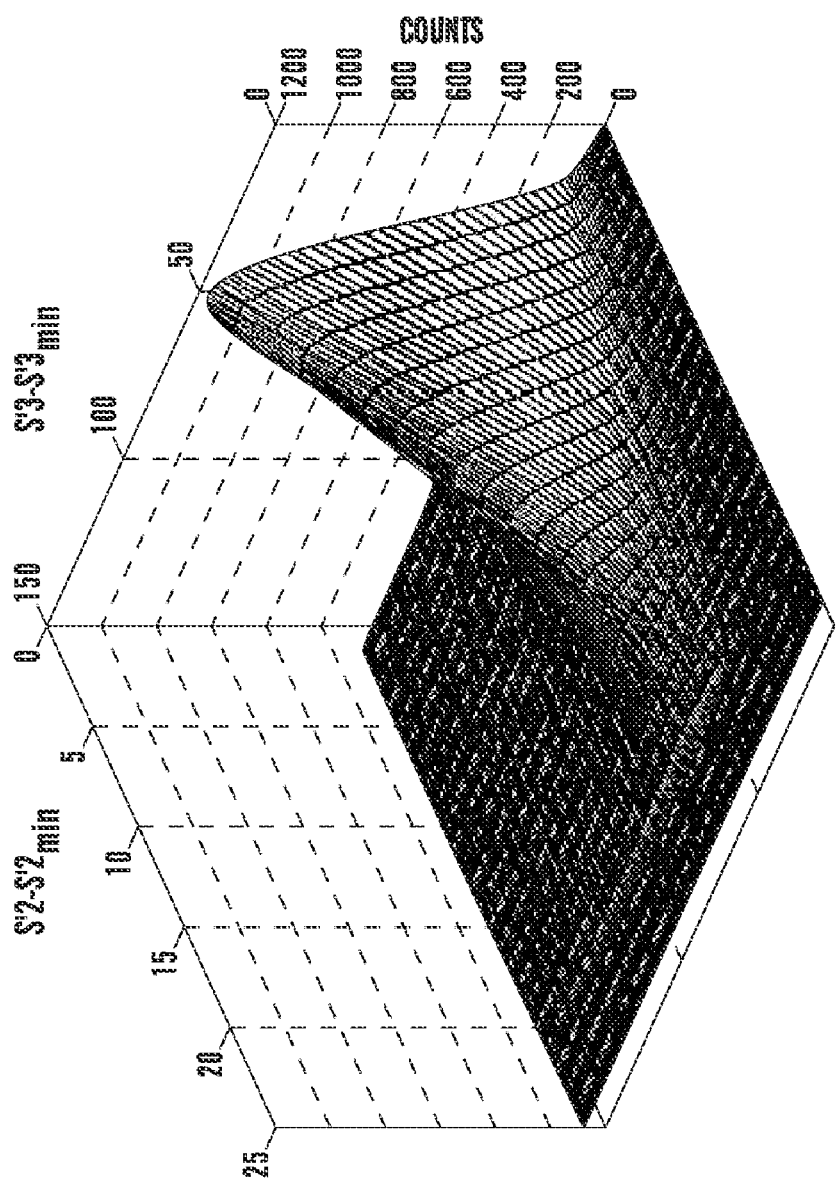

As mentioned above, D restitution contributed to conduction block by magnifying heterogeneity in I. If the D restitution function had weak dependence on I, any initial dispersion of I due to V restitution would be lessened on subsequent stimulations. FIG. 9 shows the effect of altering D restitution slope by increasing and decreasing the parameter $\tau_D$. FIG. 9A shows steady state restitution curves for four different values of $\tau_D$. The wild type model was $\tau_D$=28. As shown in FIGS. 9B and 9C, increasing $\tau_D$ led to a significantly smaller peak in the histogram, as well as fewer total instances of conduction block. Conversely, decreasing $\tau_D$, which led to a steeper steady state restitution slope, had significantly more counts (FIG. 9D). However, it is important to note that even for the $\tau_D$=40 model, which had a maximum steady state slope of 0.82, instances of type II block were found.

Example 6

Contribution of M to Conduction Block

Figure 10A:
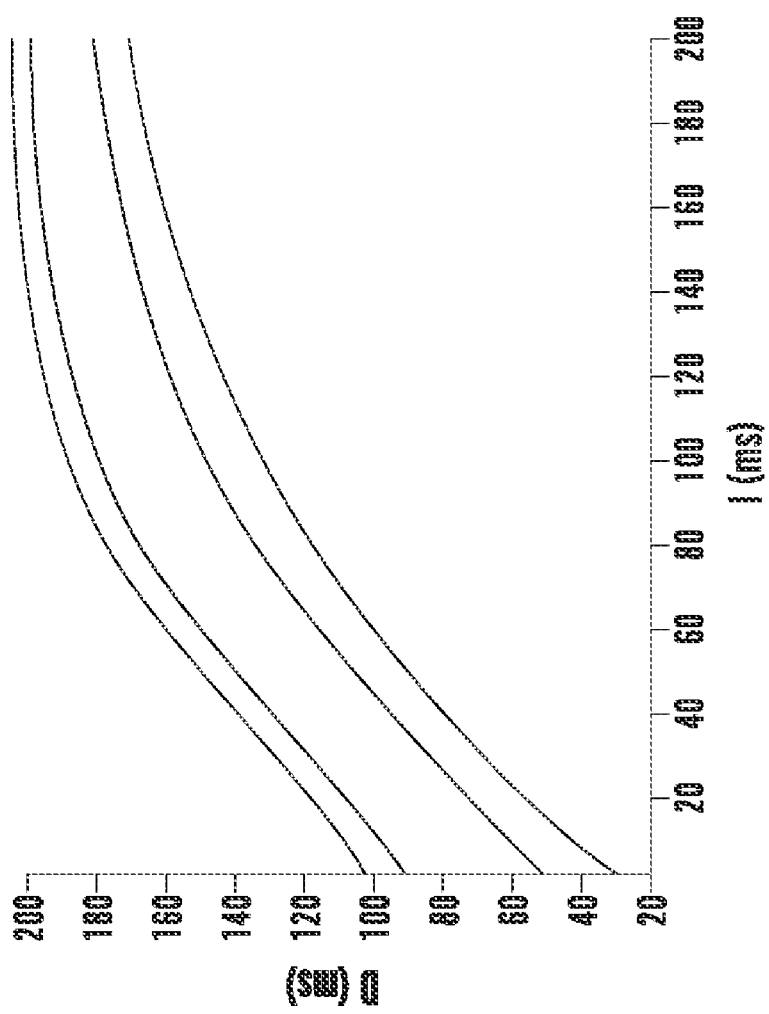
FIGS. 10A-D show the role of M in type II block.
Figure 10B:
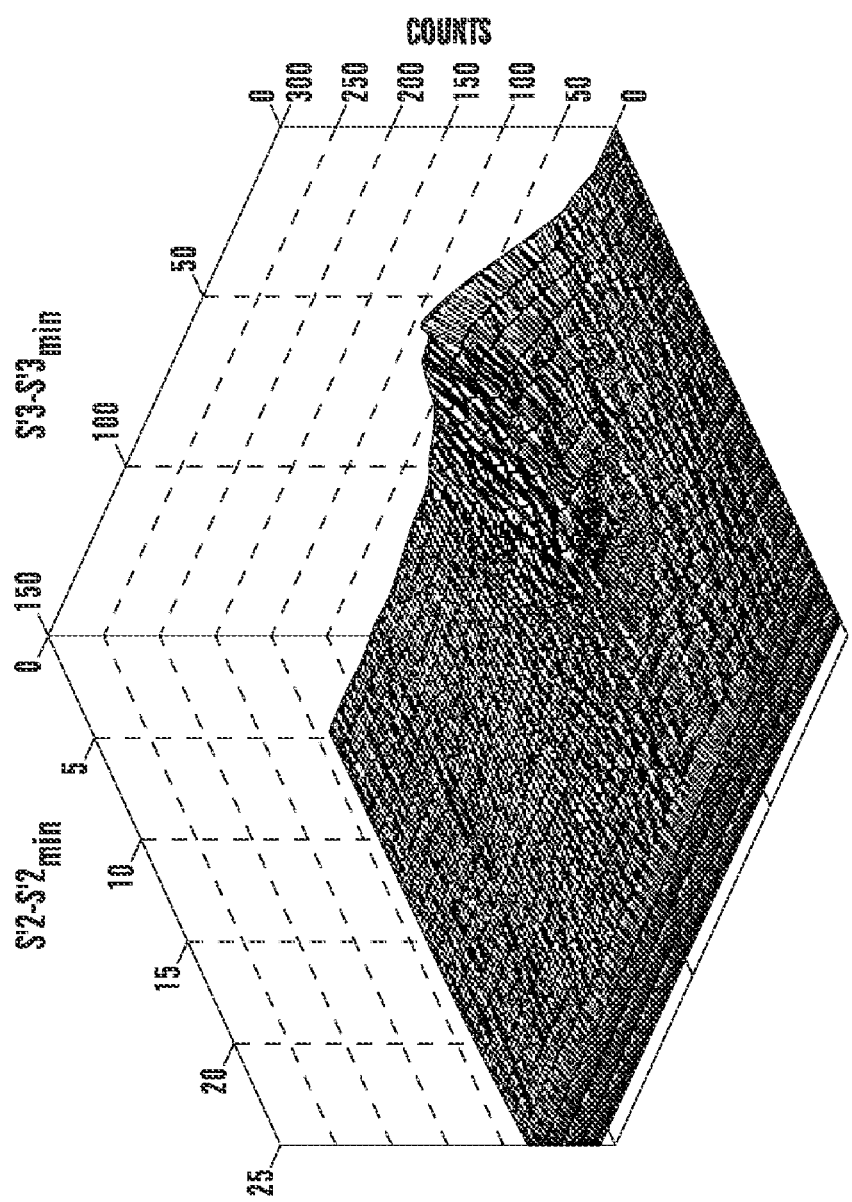
Figure 10C:
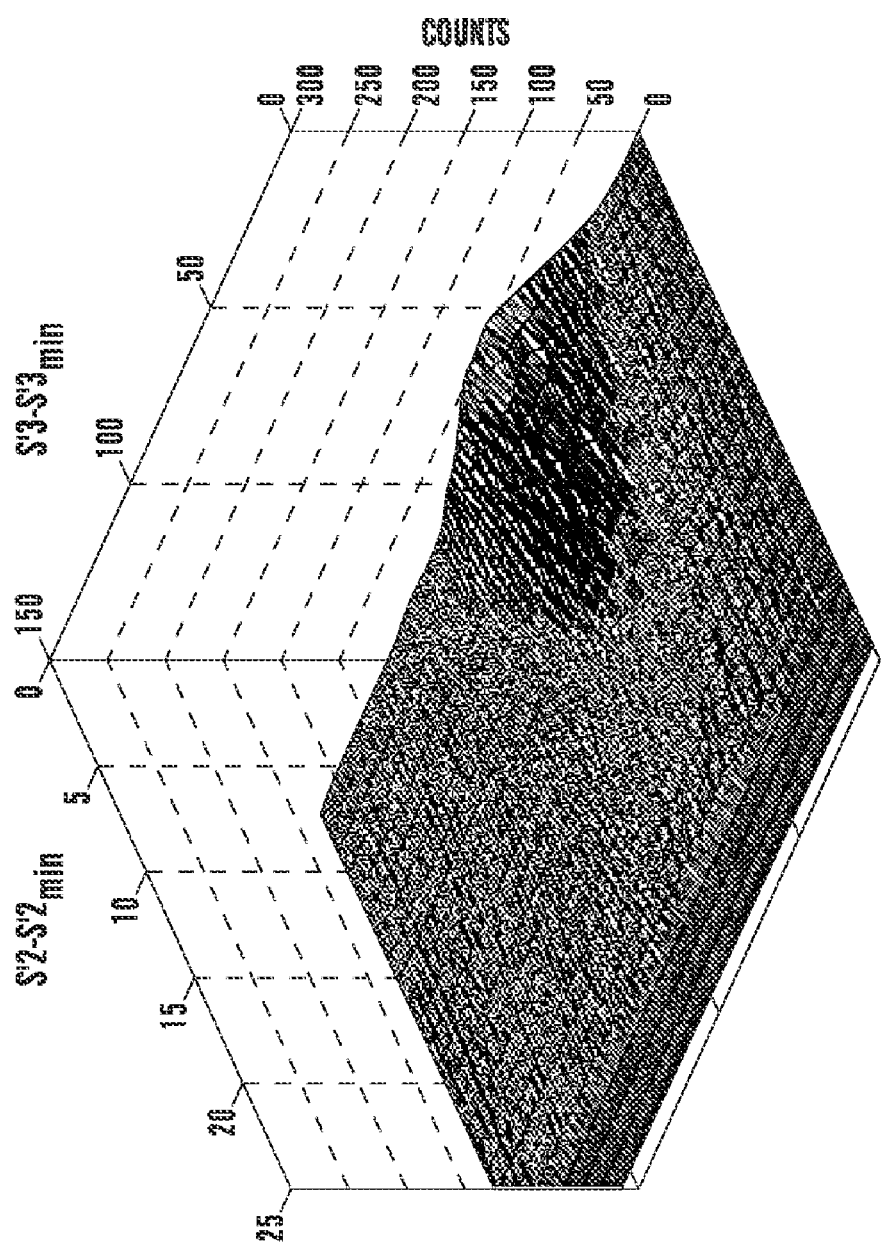
Figure 10D:
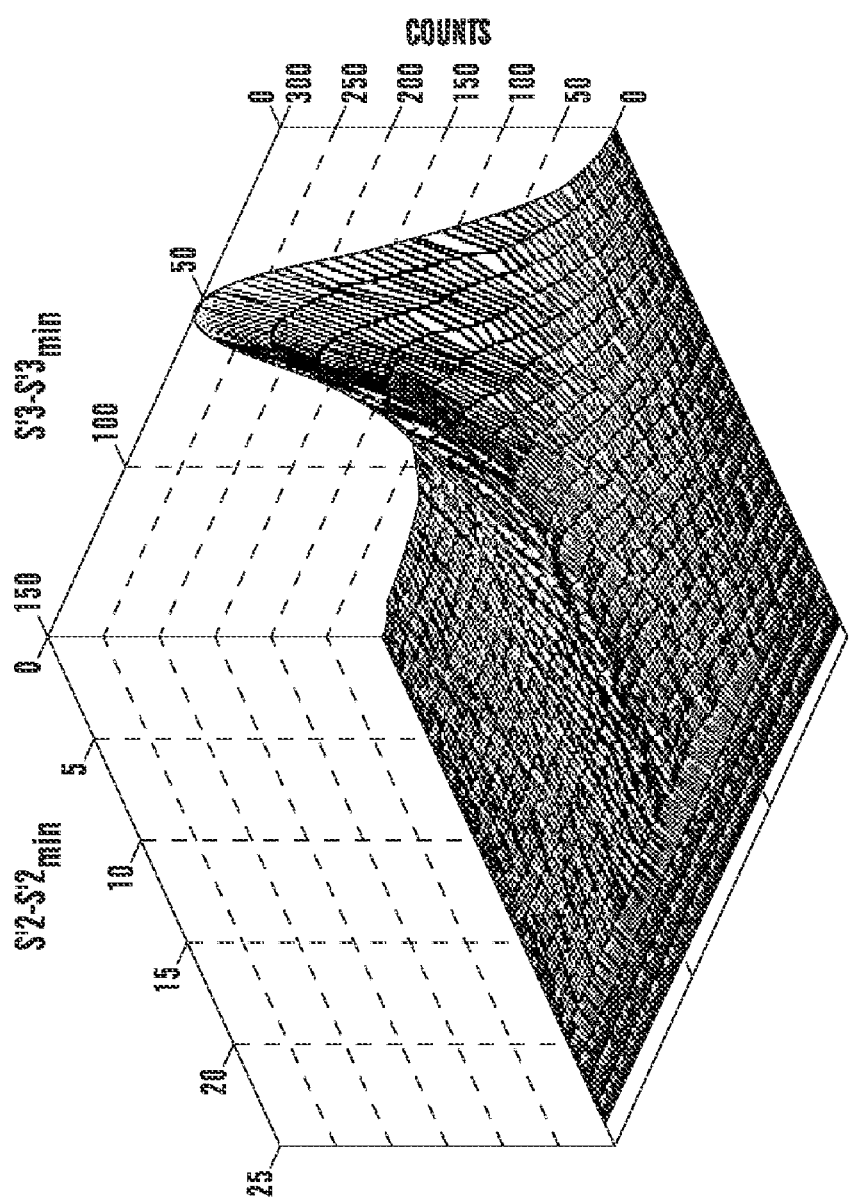

Because increasing M in the coupled maps model has been shown to eliminate steady state alternans, it was hypothesized that increasing M also would lead to fewer instances of type II block. FIG. 10 illustrates the effect of changing M on the likelihood of conduction block in the 101.10 model by increasing and decreasing the parameter $\alpha$. FIG. 10A shows steady-state restitution for four different values of $\alpha$. The wild type model was $\alpha$=0.2. In FIG. 10B, $\alpha$=0.58, which eliminated alternans but maintained a slope $\geq$1. In fact, the steady state restitution slope was 1.62, even larger than in the wild type model. In FIG. 10C, $\alpha$=0.8 and the maximum steady state restitution slope was 2.65. Both FIGS. 10B and 10C show smaller peaks and fewer total counts than the wild type model. In FIG. 10D, M was decreased ($\alpha$=0.1) and the maximum steady state slope is 1.09. The decreased memory model shows more instances of conduction block than the wild type model. This result did not depend on the magnitude of D. For example, shifting the curve from FIG. 10C by adding 70 ms to the function $f(M_{n+1}, I_n)$ did not produce more instances of type II block (in fact slightly fewer (39 229) were found). Similarly, shifting the curve from FIG. 10A down by subtracting 70 ms from $f(M_{n+1}, I_n)$ produced roughly the same number of blocks (94 151) as in FIG. 10D. Two other observations can be made. First, increasing M did not seem to be as effective as increasing $\tau_D$ in reducing the likelihood of block. Second, the steady-state D restitution function is not predictive of the likelihood of block.

Example 7

Contribution of Electronic Interactions to Conduction Block

Electronic effects have been shown to prevent alternans in some models (Cytrynbaum et al., "Stability Conditions for the Traveling Pulse: Modifying the Restitution Hypothesis," *Chaos* 12:788-99 (2002), which is hereby incorporated by reference in its entirety). Therefore, changes in electronic current may be expected to have an effect on the incidence of conduction block. The coupled maps model allowed for the complete removal of electronic interactions by eliminating the diffusion terms in equation (4). As shown in FIG. 6, the potential for conduction block was present when the previous beat generated a short-to-long pattern in I. This pattern led to a short-to-long pattern in the following D. In the wild type model, both the first and second derivative diffusion terms tended to decrease the long D and increase the short D, reducing the amount of heterogeneity and thereby reducing the likelihood of type II block. Accordingly, elimination of the diffusion terms was expected to increase the incidence of type II block and this expectation was confirmed; total counts of type II block were 88 603.

In the present invention, type II conduction block following the delivery of multiple premature stimuli was caused by the same sequence of events that caused conduction block during sustained rapid pacing in previous studies (Fox et al, "Spatiotemporal Transition to Conduction Block in Canine Ventricle," *Circ Res.* 90:289-96 (2002), which is hereby incorporated by reference in its entirety). Stimulation at a short/produced a gradient of increasing/(and, consequently, of D and V) along the fibre. The succeeding stimulus, if delivered at an appropriate interval, encountered a progressively decreasing I as it propagated down the fibre (i.e., the new wavefront encountered the waveback of the previous excitation). Thus, a short-long sequence of D at the site of stimulation was associated with the development of a long-short sequence of D at the opposite end of the fibre, similar to the pattern established during stable discordant alternans (Pastore et al., "Mechanism Linking T-Wave Alternans to the Genesis of Cardiac Fibrillation," *Circulation* 99:1385-94 (1999); Qu et al., "Mechanisms of Discordant Alternans and Induction of Reentry in Simulated Cardiac Tissue," *Circulation* 102:1664-70 (2000); and Watanabe et al., "Mechanisms for Discordant Alternans," *J Cardiovasc Electrophysiol* 12:196-206 (2001), which are hereby incorporated by reference in their entirety). When the gradient in I along the fibre was sufficiently steep in the ascending direction, the subsequent action potential encountered an I<$I_{min}$ and conduction block occurred.

Previous studies have shown that the location of the block can be predicted, given the spatial profile of D for the preceding beat (Sampson et al., "Simulation and Prediction of Functional Block in the Presence of Structural and Ionic Heterogeneity," *Am J Physiol* 281:H2597-603 (2001), which is hereby incorporated by reference in its entirety). If this information is not known, however, then developing a quantitative theory for the type II block observed with present invention becomes difficult, not only because the model consists of complicated nonlinear difference equations in both space and time, but also because the phenomenon of interest is a transient. Therefore, the usual tools of nonlinear dynamics, such as finding steady-state solutions and analyzing their stability, do not apply. Still, inspection of the defining equations produces a qualitative understanding of the results presented in this study. The mechanism for conduction block relies on three determinants. First, a non-constant V restitution function produces spatial heterogeneity in I. Next, this heterogeneity is amplified (or at least it does not decay rapidly) due to sensitive dependence of D on I. Finally, the V restitution function does not drop sufficiently close to zero at very short I, causing the wave to collide with the refractory period of the preceding excitation.

Preventing the first aspect of type II block could only be done by forcing the V restitution curve to be constant. Even in that case, type II block could still occur if there were intrinsic heterogeneity in the fibre. Therefore, the likelihood that type II block could be diminished by two different methods was explored. The first method was to alter the V restitution function so that conduction slowed at very short I, thus preventing encroachment on the refractory period. It is important to note that this method is only viable if the decrease in conduction velocity occurs at short I. Decreasing maximum conduction velocity is in fact pro-arrhythmic, because it decreases the wavelength (Fenton et al., "Multiple Mechanisms of Spiral Wave Breakup in a Model of Cardiac Electrical Activity," *Chaos* 12:852-92 (2002), which is hereby incorporated by reference in its entirety). Although selective slowing of conduction at short rest intervals may create a greater dispersion of refractoriness after a premature beat, the benefits of this intervention seem to outweigh the risks, at least under the conditions of this study. Whether a similar strategy will suppress conduction block in 2D or 3D tissue with realistic intrinsic heterogeneity remains to be determined.

The second method for reducing the likelihood of type II block was to reduce the sensitivity of D on I. If the system is uni-dimensional, this is done by decreasing the D restitution slope. The lower the slope of the D restitution relation, the lower the likelihood of spatial dispersion of repolarization secondary to dispersion of I. However, the model used in the present invention did not have a simple relationship between the slope of the steady-state D restitution function and the likelihood of block. Instead, the important quantity is the sensitivity of D to the preceding I, given by $$\gamma = \frac{df}{dI} = \frac{\partial f}{\partial I} + \frac{\partial f}{\partial M}\frac{\partial g}{\partial I}. \tag{6}$$

The quantity γ is the amplification factor relating the dispersion in D to the dispersion in the preceding I. If γ is small, then any initial dispersion in I will decay quickly. If γ is large, the dispersion of I can persist or even be amplified. It can be shown that at short cycle lengths the first term dominates, giving $$\gamma \approx \frac{\partial f}{\partial I} = (1 - \alpha M^*)\frac{B}{\tau_D}\frac{e^{-(I^*-C)/\tau_D}}{(1+e^{-(I^*-C)/\tau_D})^2}. \tag{7}$$

M* and I* are the steady state values at a given cycle length. This equation is of limited quantitative use since the system never reaches steady state (and the cycle length is continuously changing). Still, it suggests that the likelihood of block can be reduced by either increasing $\tau_D$ or by increasing α. The simulation results support this qualitative argument. This result highlights the fact that the dynamics during premature stimulation cannot be predicted from the steady-state D restitution function. In fact, the more relevant experimental measure would be the S'1-S'2 D restitution function at very short S'2. The slope of this curve at short/would directly measure the dispersion of D after a very short S'1-S'2 interval had produced some initial dispersion in I. However, relating the S'1-S'2 curve to any quantitative prediction about type II block is not straightforward.

Programmed electrical stimulation has been used extensively in the past to induce ventricular arrhythmias in patients thought to be at risk for the development of ventricular fibrillation (Anderson et al., "Clinical Value of Cardiac Electrophysiology Studies, *Cardiac Electrophysiology. From Cell to Bedside* 2$^{nd}$ edn, ed D. P. Zipes and J. Jalife (Philadelphia, Pa.: Saunders) 1133-50 (1995), which is hereby incorporated by reference in its entirety). However, the stimulation protocol used in the clinical studies differs significantly from that used here, in that arrhythmia induction was attempted using tightly coupled premature stimuli, which produced block similar to the type I block. Once the patient's arrhythmia had been induced using multiple premature stimuli, the test was repeated after administration of an antiarrhythmic drug. In many cases a drug could be found that would suppress the patient's inducible arrhythmia. Yet the results of large scale clinical trials eventually revealed that patients sent home on such medications were as or more likely to die suddenly than patients who did not receive such treatment (Cast, "Preliminary report: Effect of Encamide and Flecamide on Mortality in a Randomized Trial of Arrhythmia Suppression After a Myocardial Infarction," in *New Engl J Med* 321:406-12 (1989) and Waldo et al., "Effect of D-Sotalol on Mortality in Patients with Left Ventricular Dysfunction After Recent and Remote Myocardial Infarction. The SWORD Investigators. Survival With Oral D-Sotalol," *Lancet* 348:7-12 (1996), which are hereby incorporated by reference in their entirety). Clearly, the induction of arrhythmias using this particular stimulation protocol was not predictive of the development of ventricular fibrillation.

The failure of the standard method of programmed stimulation to accurately assess vulnerability to ventricular fibrillation may relate to the fact that this method was designed primarily to induce conduction block and re-entry by perturbing intrinsic heterogeneity. The potential contribution of dynamic heterogeneity to the development of conduction block would not be assessed adequately using such a protocol. In addition, interventions that were intended to prevent the induction of arrhythmias using the standard protocol, such as slowing of conduction or prolongation of refractoriness, might be effective in that regard, secondary to a reduction in intrinsic heterogeneity, but might not reduce dynamic heterogeneity. Consequently, the beneficial effects of such interventions on arrhythmias induced by the standard stimulation protocol might not correspond to a reduction in the incidence of ventricular fibrillation, if induction of the latter is influenced importantly by dynamic heterogeneity.

Dynamically induced heterogeneity and conduction block is one of many potential mechanisms for spiral break-up in cardiac tissue (see for example (Fenton et al., "Multiple Mechanisms of Spiral Wave Breakup in a Model of Cardiac Electrical Activity," Chaos 12:852-92 (2002), which is hereby incorporated by reference in its entirety)). Because wave propagation in the heart is extremely complex and influenced by many factors, it is unlikely that only one mechanism is responsible for induction and maintenance of all cardiac arrhythmias. Nevertheless, the results of this study suggest several potential interventions that may reduce the probability of arrhythmia induction, including flattening the D restitution slope, decreasing V at short I and increasing M. There is experimental support for the idea that flattening D restitution suppresses ventricular fibrillation (Riccio et al., "Electrical Restitution and spatiotemporal Organization During Ventricular Fibrillation," Circ Res 84:955-63 (1999), which is hereby incorporated by reference in its entirety), but altering V and M with the objective of preventing ventricular fibrillation has not been attempted. Tests of these options may not be likely in the near future; however, given that drugs that increase the recovery of sodium channels at depolarized potentials are not currently available, and alteration of M may not be possible until the ionic basis for this phenomenon has been established. Nevertheless, judicious alterations of D, V, and M may hold future promise for new and more effective therapies for ventricular fibrillation Example 8

Map Recordings of Beagle Right and Left Ventricles

Figure 11:
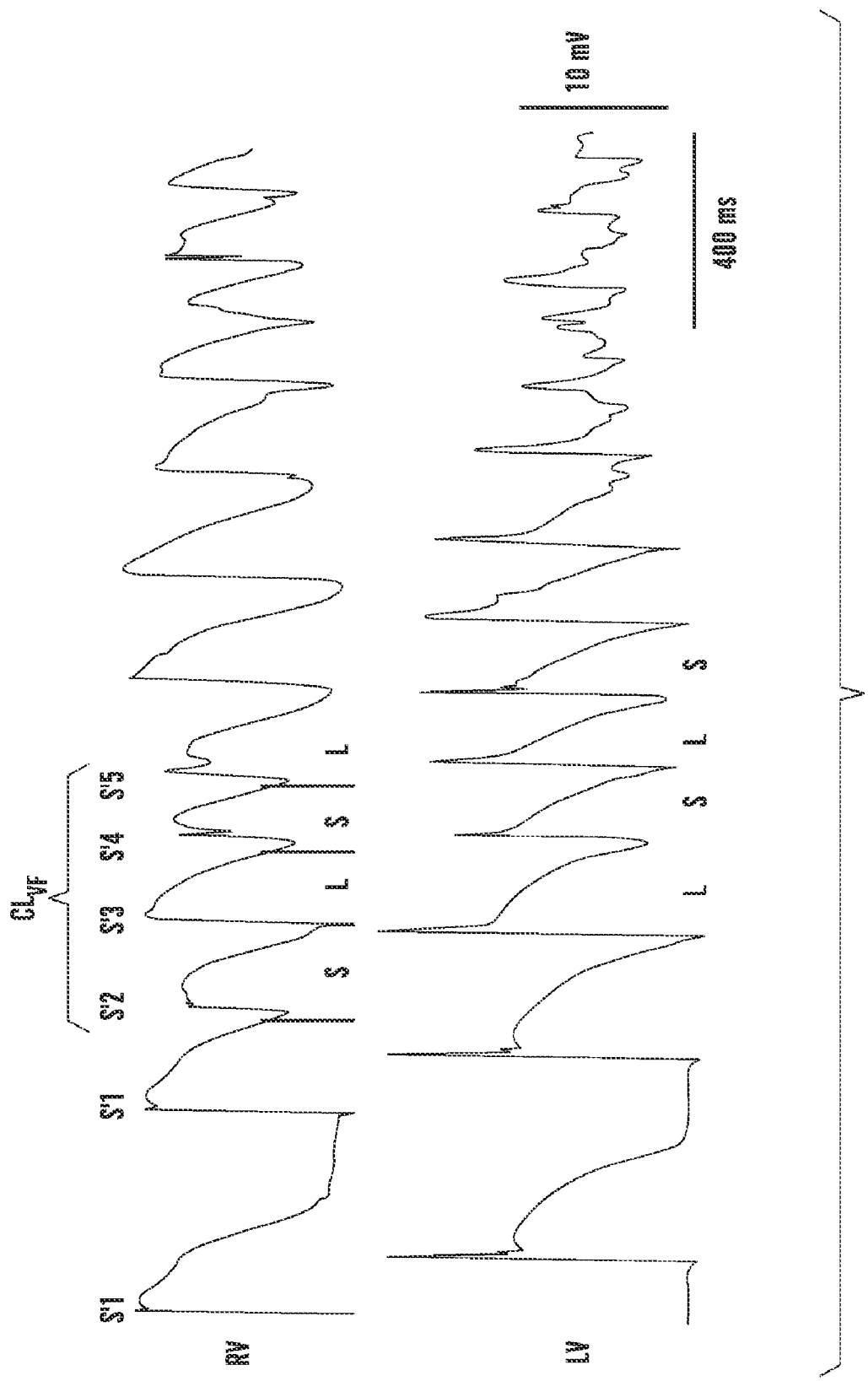
FIG. 11 shows examples of MAP recordings obtained from the right (RV) and left (LV) ventricles of a closed-chest anesthetized beagle during delivery of multiple premature stimuli ($CL_{VF}$) to the RV. $CL_{VF}$ were chosen to produce maximum dynamically-induced dispersion of repolarization, as predicted from the results of the coupled maps model shown in FIG. 7.

More recently, investigations as to whether dynamically-induced spatial dispersion of repolarization promotes the development of conduction block and reentrant excitation in settings where underlying intrinsic heterogeneity is present were initiated. To that end, the sequence of premature stimulus intervals predicted by the computer model to cause conduction block was delivered to the right ventricles of closed chest anesthetized normal beagles and MAP recordings were obtained from the right and left ventricles. The dogs initially were paced at a cycle length of 400 ms and a single premature stimulus ($S'_2$) was delivered at progressively shorter $S'_1S'_2$ intervals until $S'_2$ failed to capture ($S'_1S'_{2min}$). The $S'_1S'_2$ interval was then set to $S'_1S'_{2min}+40$ ms, and an $S'_3$ stimulus was delivered at progressively shorter $S'_2S'_3$ intervals until $S'_{3min}$ was encountered. The procedure was then repeated to find $S'_{4min}$ and $S'_{5min}$. Thereafter, a sequence of premature stimuli consisting of $S'_1S'_{2min}+5$ ms, $S'_2S'_{3min}+50$ ms, $S'_3S'_{4min}+5$ ms and $S'_4S'_{5min}+5$-10 ms was delivered. As shown in FIG. 11, the patterns of APD produced by this sequence of premature cycle lengths ($CL_{VF}$) was similar to that produced in the computer models (c.f. FIG. 5). Short duration responses (S) at the RV recording site were associated with longer duration responses (L) at the LV site and vice versa and the pattern of discordant alternans preceded the development of VF.

Figure 12:
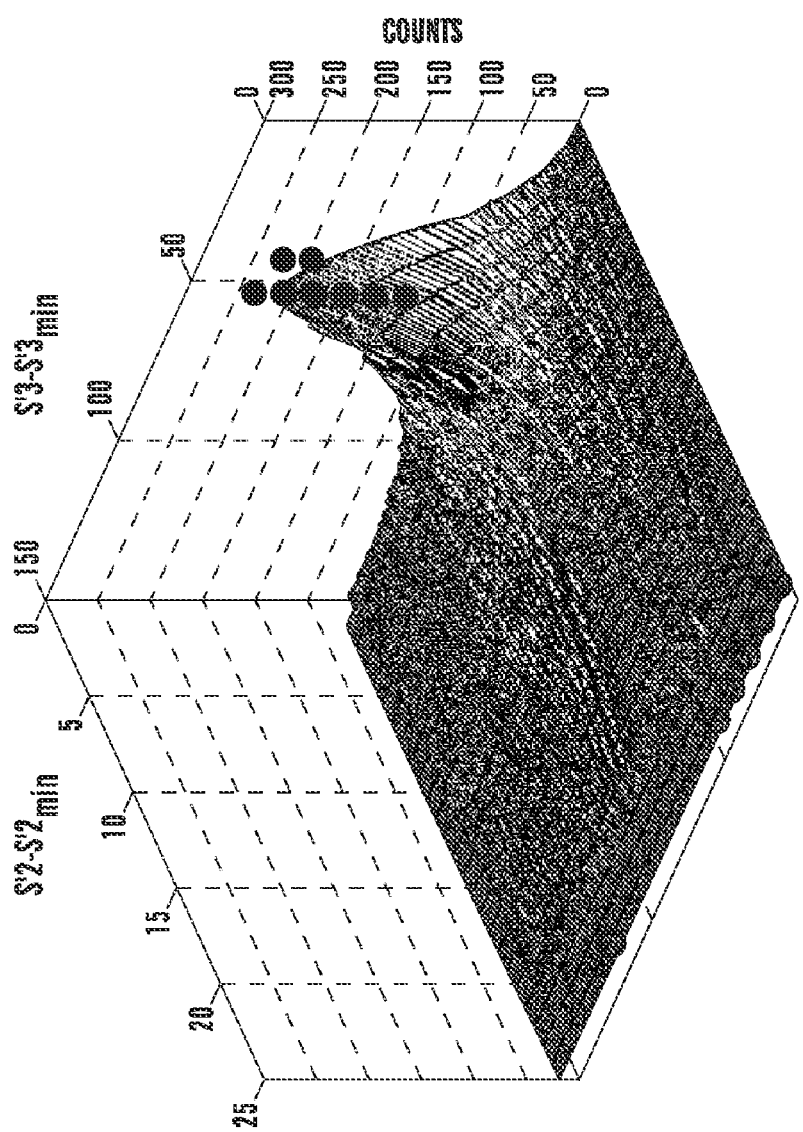
FIG. 12 shows the incidence of conduction block in Beagles. The incidence of conduction block followed the delivery of 4 premature stimuli in the coupled maps memory model (FIG. 7), and following the delivery of $CL_{VF}$ in anesthetized beagles (filled circles). $CL_{VF}$ induced VF in all 8 dogs. In contrast, patterns of cycle lengths that fell outside $CL_{VF}$ did not induce VF (unfilled circles).

The delivery of $CL_{VF}$ has produced VF in all 8 dogs tested thus far, whereas the delivery of multiple premature stimuli at sequentially shorter cycle lengths has failed to induce VF in any of the dogs (FIG. 12). Although, for obvious reasons, not all 67,000 possible combinations of cycle lengths predicted to cause conduction block in the model, nor more than a few of the intervals that are not expected to cause block were tested, the highly reproducible induction of VF by $CL_{VF}$ lying near the peak of the plot shown in FIG. 11 suggests that stimulus protocols designed to maximize dynamically-induced spatial heterogeneity of repolarization may reliably promote the induction of VF. The exact nature of the spatial dispersion produced by such a protocol will require more extensive mapping than can be accomplished by two MAP recordings, but the observation that $CL_{VF}$ produces discordant alternans between at least 2 RV and LV recording sites suggests that the pattern of APD generated by the computer models may pertain to the intact heart.

As a further test of the hypothesis that dynamically-induced spatial heterogeneity is arrhythmogenic, it was determined whether a reduction in the slope of the APD restitution relation suppresses the development of spatial heterogeneity APD and conduction block during premature stimulation, as shown in the computer model (Fox et al., Dynamic Mechanism for Conduction Block in Heart Tissue," New J Phys. 5:101.1-101.14 (2003), which is hereby incorporated by reference in its entirety). For these studies, the effects of verapamil, which is known to decrease the slope of the dynamic restitution relation (Riccio et al., "Electrical Restitution and Spatiotemporal Organization During Ventricular Fibrillation," Circ Res 84:955-63 (1999), which is hereby incorporated by reference in its entirety), in the anesthetized closed chest dogs described above (n=8) were tested. MAP duration (MAPD) was measured in RV and LV endocardium during programmed stimulation of the RV using 4 appropriately timed premature stimuli ($S'_2$-$S'_5$), following a train of 20 stimuli at a constant $S'_1S'_1$ interval of 400 ms. The stimulation protocol incorporated the same short-long-short-intermediate sequence shown in FIG. 12, adjusted as necessary to account for changes in $S'_{2min}$-$S'_{5min}$ produced by verapamil. VF induction was attempted during control and 30 minutes after i.v. verapamil (0.1, 0.3 or 1.0 mg/kg/min).

VF induction occurred in all dogs during control and after 0.1 mg/kg verapamil and was associated with discordant alternans of MAPD between RV and LV. In contrast, after the two higher verapamil doses MAPD alternans was reduced in magnitude and was concordant and VF could not be induced. These effects were not associated with significant changes in the slope of the standard ($S'_1S'_2$) MAPD restitution relation, which was 0.41±0.17 during control and was 0.47±0.28, 0.56±0.20 and 0.39±0.18 after verapamil. Thus, suppression of spatial APD heterogeneity by verapamil was associated with an inability to induce VF using premature stimuli. However, the doses of verapamil required to produce this effect had significant negative dromotropic, chronotropic and inotropic effects: verapamil increased the PR interval (from 84.7±3.8 during control to 111.8±12.2, 132.0±15.0 and 139.5±18.0 ms after verapamil), decreased heart rate (from 139.0±9.7 to 110.0±2.1, 101.6±3.8, and 95.2±8.8 bpm) and decreased mean blood pressure (from 116.8±7.3 to 107.4±11.4, 108.0±6.3 and 101.2±9.4 mmHg). These results suggest that suppression of VT-induced spatial electrical heterogeneity may be one means of preventing VF, but that verapamil is unlikely to be the drug of choice for producing such an effect in patients.

Example 9

Ventricular Fibrillation in German Shepherd Dogs

Figure 13:
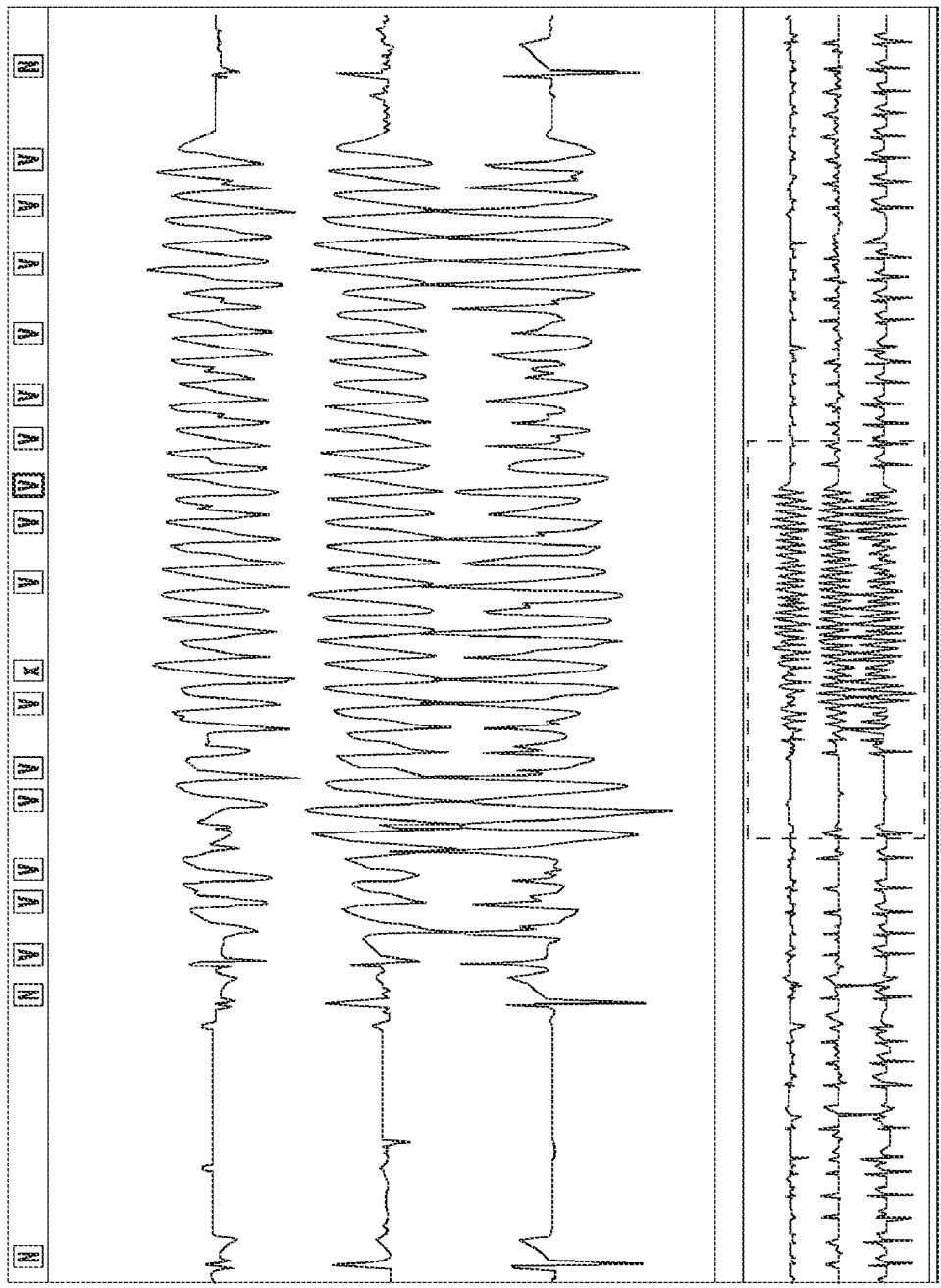
FIG. 13 shows the spontaneous non-sustained polymorphic ventricular tachycardia in a German Shepherd dog.

Although the induction of VF by $CL_{VF}$ in normal beagles confirms the predictions made by the computer models, this result is somewhat expected, in that the data used to construct the models was obtained from normal canine myocardium. This model has the additional limitation of requiring external stimuli to induce VF, since these dogs do not have spontaneous ectopy. To test the predictions from the computer model more rigorously, next it was investigated whether $CL_{VF}$ induced VF in German shepherd dogs that display non-sustained polymorphic VT and have an inherited predisposition to sudden death (FIG. 13). As discussed above, one of the interesting and unanswered questions with respect to these animals is why they often live for months with multiple episodes of rapid, polymorphic VT before succumbing to sudden death. Based on the response of the beagles to $CL_{VF}$, it seems possible that the German shepherds, despite having copious amounts of ectopy, do not die sooner, because they do not routinely generate the proper sequence of coupling intervals, insofar as promoting dynamically-induced spatial dispersion of repolarization is concerned.

Figure 18:
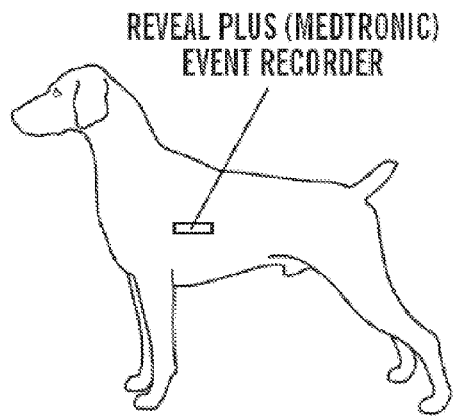
FIG. 18 is a schematic illustration of a Reveal Plus (Medtronic) event recorder implanted in a German Shepherd dog.

As an initial test of this idea, 5 affected German shepherd dogs were anesthetized and instrumented as described above for the beagles. $CL_{VF}$ were determined from measurements of $S'_{2min}$-$S'_{5min}$ and predictions from the beagle-based computer model and were delivered to the RV or LV. VF was induced in 3 of the dogs, but not in the other two, even after several adjustments of the $CL_{VF}$. Sequences of cycle lengths obtained from Holter recordings during multiple episodes of polymorphic VT ($CL_{VT}$) also were delivered to the dogs. None of these sequences induced VF. The sequences during $CL_{VT}$ consisted of progressively shorter cycle lengths, in contrast to $CL_{VF}$, which were short-long-short-short. In addition, even during longer runs of non-sustained VT, such as the run shown in FIG. 13, a $CL_{VF}$-type pattern did not occur. This observation raises the question of why do the German shepherds eventually die suddenly? Unfortunately, despite the hundreds of Holter recordings obtained since this colony was established, VF has never been captured. To remedy this situation, Reveal Plus© (Medtronic) event recorders were implanted in severely affected dogs (see FIG. 18). Thus far, the development of VF in one dog has been captured. The sequence of cycle lengths preceding VF was similar to that used to precipitate VF in the programmed stimulation studies, but clearly more episodes of spontaneous VF need to be captured and analyzed before definitive conclusions can be drawn.

Example 10

Calcium Channel Agonists and Ventricular Fibrillation

Figure 14B:
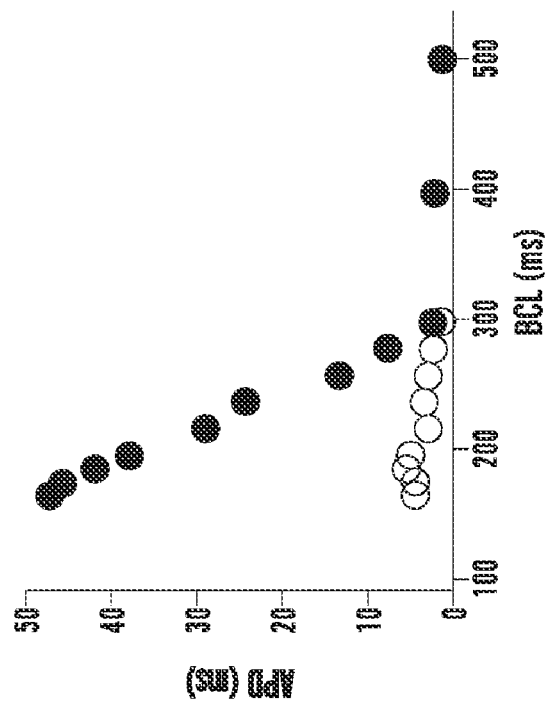
FIGS. 14A-C show the effects of verapamil on action potential duration (APD) restitution and ventricular fibrillation (VF).
Figure 14A:
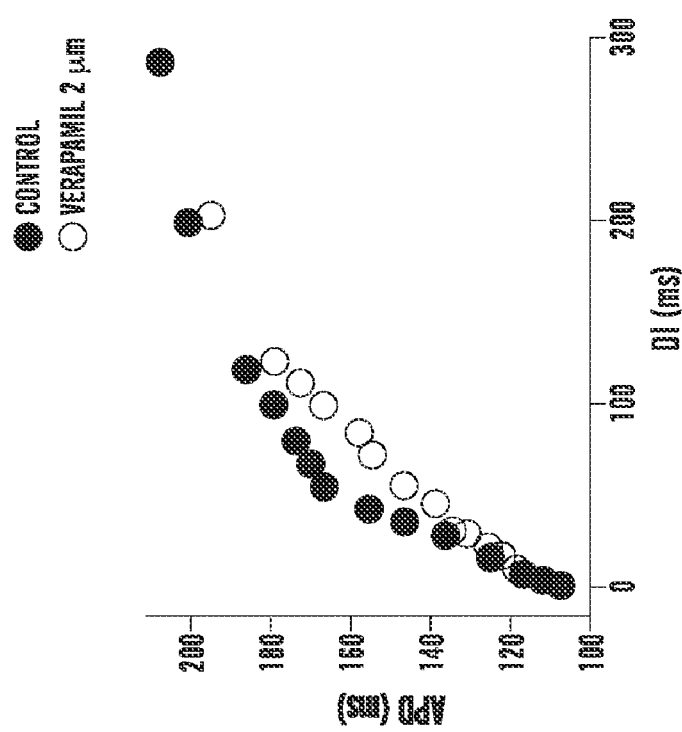
Figure 14C:
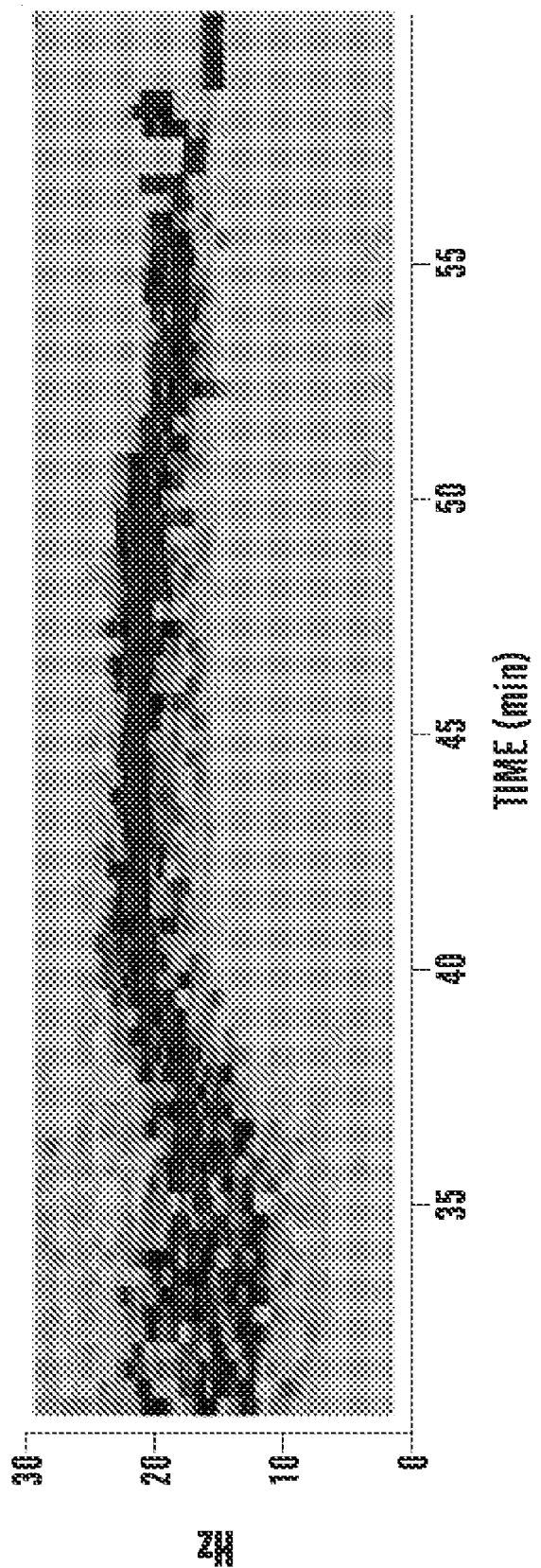

The suppression of VF by verapamil, in association with a reduction in the slope of the APD restitution relation, (FIG. 14) suggests that the L-type calcium current ($I_{Ca}$) plays a key role in restitution and in the development of VF (Riccio et al., "Electrical Restitution and Spatiotemporal Organization During Ventricular Fibrillation," *Circ Res* 84:955-963 (1999) and Chudin et al., "Intracellular $Ca^{2+}$ Dynamics and the Stability of Ventricular Tachycardia," *Biophys J* 77:2930-2941 (1999), which are hereby incorporated by reference in their entirety). To better define these roles, an ionic model was developed for the cardiac ventricular myocyte (CVM) based on the Winslow (Winslow et al., "Mechanisms of Altered Excitation-Contraction Coupling in Canine Tachycardia-Induced Heart Failure, II.," *Circ Res* 84:571-586 (1999), which is hereby incorporated by reference in its entirety) and Luo-Rudy models (Luo et al., "A Dynamic Model of the Cardiac Ventricular Action Potential, I: Simulation of Ionic Currents and Concentration Changes," *Circ Res* 74:1071-1096 (1994), which is hereby incorporated by reference in its entirety) that generates physiologically realistic APD alternans over a wide range of pacing cycle lengths (Fox et al., "Ionic Mechanism of Cardiac Alternans," *Am J Physiol* 282:H516-H530 (2002), which is hereby incorporated by reference in its entirety). Using this model, the L-type $Ca^{2+}$ current was implicated as an important determinant of APD alternans, according to the mechanism shown in FIG. 15. Upon initiation of pacing at a short CL, $I_{Ca}$ is fully recovered prior to the first action potential and activates fully during the action potential, which results in a long APD. The long action potential subsequently is followed by a short diastolic interval, during which $I_{Ca}$ fails to recover completely from $Ca^{2+}$-induced inactivation. Because of decreased availability of $I_{Ca}$, the duration of the subsequent action potential is shorter, which results in a longer succeeding diastolic interval, more complete recovery of $I_{Ca}$ and a long action potential duration. This cycle then repeats, eventually establishing a steady-state alternans of $I_{Ca}$ and APD.

Example 11

Potassium Channel Agonists and Ventricular Fibrillation

Figure 15B:
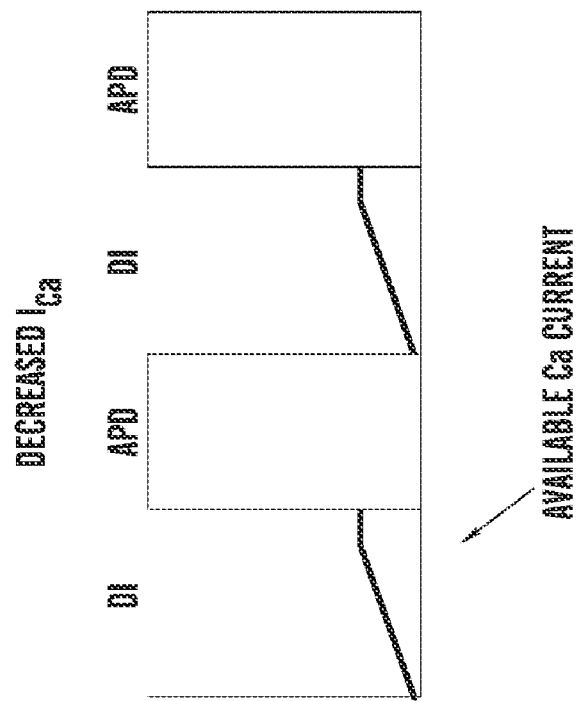
FIGS. 15A-B show the putative mechanism for APD alternans and the suppression of alternans by calcium channel blockade. Under control conditions, alternation of the length of the diastolic intervals (DI) during APD alternans causes alternation of the magnitude of $I_{Ca}$, secondary to incomplete recovery of $I_{Ca}$ from inactivation during the short DI (FIG. 15A). Reduction of $I_{Ca}$ decreases APD, which prolongs DI, so that DI following each APD is sufficiently long to allow complete recovery of $I_{Ca}$ (FIG. 15B). In the absence of alternations of $I_{Ca}$, APD alternans in suppressed.
Figure 15A:
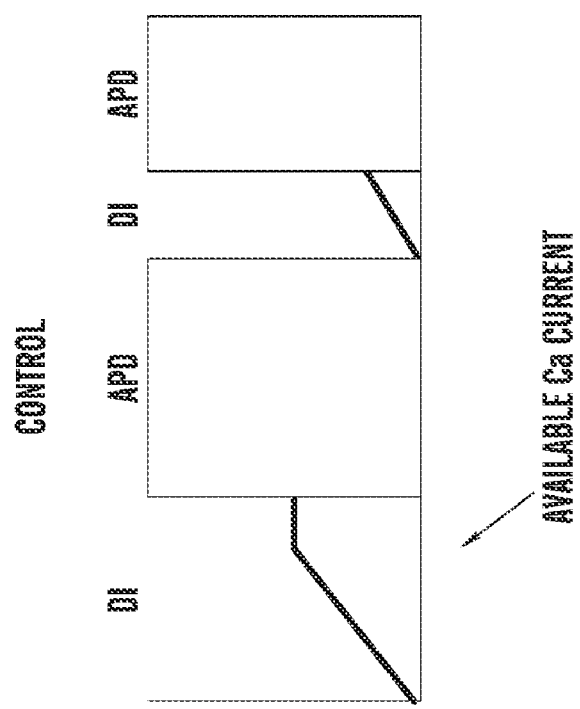
Figure 16A:
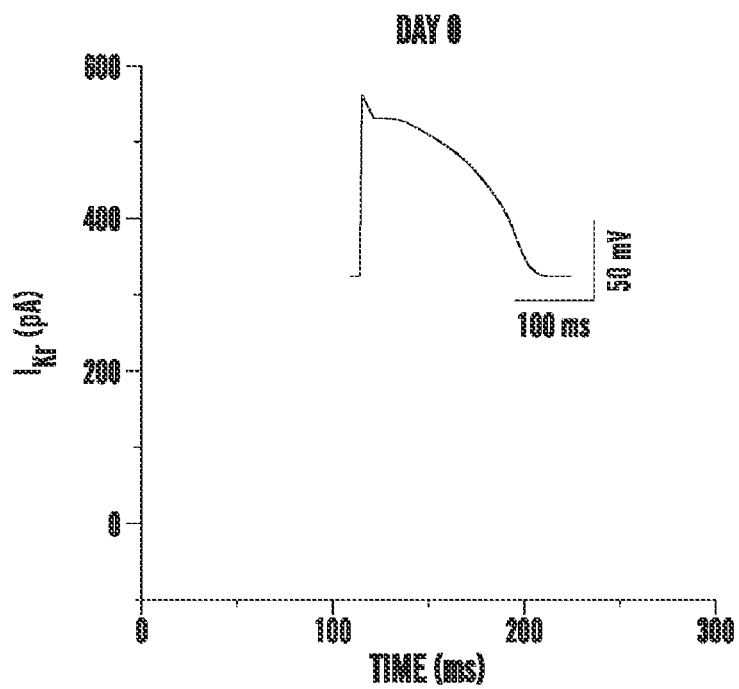
FIGS. 16A-D show the effects of HERG overexpression on $I_{Kr}$ and APD alternans in isolated canine cardiac myocytes. Current traces of $I_{Kr}$ (FIG. 16A) and action potentials during pacing at CL=200 msec (FIG. 16B) were obtained from myocytes in the day of isolation (Day 0). Current traces of $I_{Kr}$ (FIG. 16C) and action potentials during pacing at CL=200 msec (FIG. 16D) were obtained from myocytes after 3 days in cell culture and infection with adenovirus (Day 3+HERG). HERG overexpression increased $I_{Kr}$ and suppressed APD alternans.
Figure 16B:
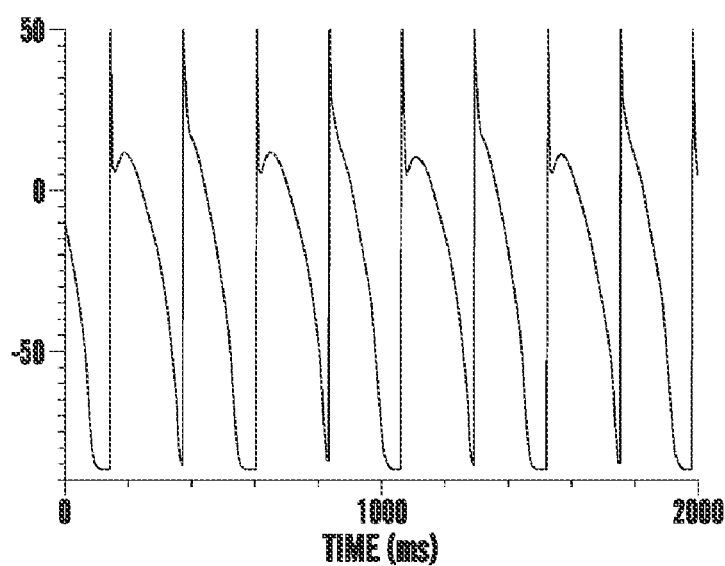
Figure 16C:
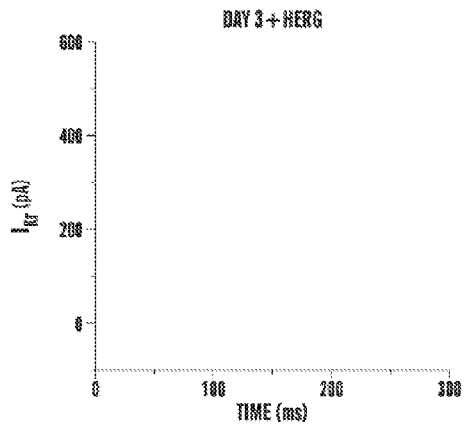
Figure 16D:
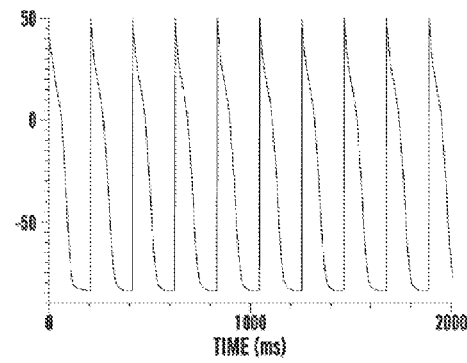

From the mechanism for APD alternans outlined in FIG. 15, it was anticipated that shortening of APD during rapid pacing will prolong DI, which, in turn, might provide adequate time for complete recovery of $I_{Ca}$. If so, reducing the magnitude of APD alternans could be accomplished by increasing outward repolarizing currents, rather than by decreasing $I_{Ca}$. This idea has been supported by additional computer modeling studies in which APD alternans was suppressed by increasing any one of several outward repolarizing currents (e.g., the rapid ($I_{Kr}$) and slow ($I_{Ks}$) components of the delayed rectifier and the inward rectifier ($I_{K1}$)) (Fox et al., "Ionic Mechanism of Cardiac Alternans," *Am J Physiol* 282: H516-H530 (2002), which is hereby incorporated by reference in its entirety). Although agonists for these currents generally are not available, it might be possible to modify currents such as $I_{Kr}$ and $I_{Ks}$ by increasing phosphatidyl inositol bisphosphate (PIP2) levels (Bian et al., "HERG K-Channel Activity is Regulated by Changes in Phosphatidyl Inositol 4,5-Bisphosphate," *Circ Res* 89:1168-1176 (2001), which is hereby incorporated by reference in its entirety) or by altering the phosphorylation state of the channels (Kiehn, J., "Regulation of the Cardiac Repolarizing HERG Potassium Channel by Protein Kinase A," *Trends Cardiovasc Med* 10:205-209 (2001); Heath et al., "Protein Kinase C Enhances the Rapidly Activated Delayed Rectifier Potassium Current, $1_{Kr}$, Through a Reduction in C-Type Inactivation in guinea Pig Ventricular Myocytes,"*J Physiol* 522:391-402 (2000); Marx et al., "Requirement of a Macromolecular Signaling Complex for β Adrenergic Receptor Modulation of the KCNQ1-KCNE1 Potassium Channel," *Science* 295:496-499 (2002), which are hereby incorporated by reference in their entirety), provided the channels can be phosphorylated without concomitant phosphorylation of calcium channels or can be upregulated in the presence of a calcium channel antagonist, to offset increased $I_{Ca}$ secondary to phosphorylation (Reuter et al., "The Regulation of Calcium Conductance of Cardiac Muscle by Adrenaline," *J Physiol* 246:49-62 (1977), which is hereby incorporated by reference in its entirety).

Recently, increasing $I_{Kr}$ as an approach to suppressing APD alternans has been examined. $I_{Kr}$ plays an important role in cardiac repolarization, increasing to a maximum during phase 3 of the action potential, as the channel recovers from inactivation, and then decreasing, as the electrical driving force decreases and as deactivation of the channel increases (Sanguinetti et al., "Two Components of Cardiac Delayed Rectifier K+ Current. Differential Sensitivity to Block by Class III Antiarrhythmic Agents," *J Gen Physiol* 96:195-215 (1990); Rocchetti et al., "Rate Dependency of Delayed Rectifier Currents During the Guinea Pig Ventricular Action Potential," *J Physiol* 534:721-732 (2001); Gintant, G., "Characterization and Functional Consequences of Delayed Rectifier Current Transient Repolarization," *Am J Physiol* 278: h806-H817 (2000); Gintant, G., "Regional Differences in $I_K$ Density in Canine Left Ventricle: Role of $I_{Ks}$ in Electrical Heterogeneity," *Am J Physiol* 268:H604-H613 (1995); and Clay et al., "A Quantitative Description of the E-4031-Sensitive Repolarization Current in Rabbit Ventricular Myocytes, "*Biophys J* 69:1830-1837 (1995), which are hereby incorporated by reference in their entirety). Because $I_{Kr}$ contributes minimally to the action potential plateau, increasing $I_{Kr}$ may have little or no effect on the $Ca^{2+}$ transient. Consequently, by increasing $I_r$ it may be possible to suppress APD alternans without adversely affecting contractility.

At present, however, there are no $I_{Kr}$ agonists available to test this hypothesis. To circumvent this problem, isolated ventricular myocytes were infected with an adenovirus expressing HERG, the gene that encodes the pore-forming domain of $I_{Kr}$, to increase HERG protein expression level and the corresponding $I_r$ current (Nuss et al., "Overexpression of a Human Potassium Channel Suppresses Cardiac Hyperexcitability in Rabbit Ventricular Myocytes," *J Clin Invest* 103: 889-896 (1999); and Waldo et al., "Effect of D-Sotalol on Mortality in Patients With Left Ventricular Dysfunction After Recent and Remote Myocardial Infarction. The SWORD Investigators. Survival with Oral D-Sotalol," *Lancet* 348:7-12 (1996), which are hereby incorporated by reference in their entirety). After verifying that $I_{Kr}$ had increased post-infection, the myocytes were paced at rapid rates to determine whether increasing $I_{Kr}$ by overexpressing HERG suppressed APD alternans. As shown in FIG. 16, over expression of HERG markedly increased $I_{Kr}$, as recorded during action potential clamp, and suppressed APD alternans during rapid pacing. Over expression of HERG did not, however, significantly reduce $I_{Ca}$, suggesting that this approach to suppression of alternans need not be accompanied by a reduction in contractility.

The current paradigm regarding $I_{Kr}$ and VF is that blocking $I_{Kr}$ is expected be anti-arrhythmic, secondary to prolongation of APD and refractoriness [Waldo et al., "Effect of D-Sotalol on Mortality in Patients With Left Ventricular Dysfunction After Recent and Remote Myocardial Infarction. The SWORD Investigators. Survival with Oral D-Sotalol. *Lancet* 348, 7-12 (1996); Hondeghem et al., "Class III Antiarrhythmic Agents Have a Lot of Potential But a Long Way to Go. Reduced Effectiveness and Dangers of Reverse Use Dependence," *Circulation* 81:686-690 (1990), which are hereby incorporated by reference in their entirety]. However, this approach has not been successful in preventing VF and, moreover, is associated with pro-arrhythmia [Waldo et al., "Effect of D-Sotalol on Mortality in Patients With Left Ventricular Dysfunction After Recent and Remote Myocardial Infarction. The SWORD Investigators. Survival with Oral D-Sotalol. *Lancet* 348, 7-12 (1996), which is hereby incorporated by referenced in its entirety]. Prolongation of APD, as reflected by an increased duration of the QT interval on the ECG, and an increase in the incidence of ventricular arrhythmias also are associated with the administration of numerous non-cardiac drugs that block $I_{Kr}$ [Mohammad et al., "Blockage of the HERG Human Cardiac K+ Channel by the Gastrointestinal Prokinetic Agent Cisapride," *Am. J. Physiol.* 723:H2534-H2538 (1997); Roy et al., "HERG, a Primary Human Ventricular Target of the Nonsedating Antihistamine Terfenadine," *Circulation* 94:815-823 (1996); Mitcheson et al., "A Structural Basis For Drug-Induced Long QT Syndrome," *Proc. Natl. Acad. Sci. U.S.A.* 97:12329-12333 (2000); Mitcheson et al., "A Structural Basis For Drug-Induced Long QT Syndrome," *Proc. Natl. Acad. Sci. U.S.A.* 97:12329-12333 (2000), which are hereby incorporated by reference in their entirety]. Similarly, inherited loss-of-function mutations in $I_{Kr}$ are accompanied by a prolongation of the QT interval and by an increased risk of lethal ventricular tachyarrhythmias such as torsade de pointes [Keating et al., "Molecular Genetic Insights Into Cardiovascular Disease," *Science* 272:681-685 (1996); Curran et al., "A Molecular Basis For Cardiac Arrhythmia: HERG Mutations Cause Long QT Syndrome," *Cell* 80:795-803 (1995); Roden et al., "A Plethora of Mechanisms in the HERG-Related Long QT Syndrome. Genetics Meets Electrophysiology," *Cardiovasc. Res.* 44:242-246 (1999); Sanguinetti, et al., "A Mechanistic Link Between An Inherited and An Acquired Cardiac Arrhythmia: HERG Encodes the $I_{Kr}$ Potassium Channel," *Cell* 81:299-307 (1995), which are hereby incorporated by reference in their entirety].

The cardiac arrhythmias associated with inherited or drug-induced abnormalities of $I_{Kr}$ are thought to be precipitated primarily by bradycardia-induced prolongation of repolarization [Keating et al., "Molecular Genetic Insights Into Cardiovascular Disease," *Science* 272:681-685 (1996); Curran et al., "A Molecular Basis For Cardiac Arrhythmia: HERG Mutations Cause Long QT Syndrome," *Cell* 80:795-803 (1995), which are hereby incorporated by reference in their entirety]. The potential mechanisms by which $I_{Kr}$ may facilitate the induction of arrhythmias at slow heart rates have been studied extensively [Hondeghem et al., "Class III Antiarrhythmic Agents Have a Lot of Potential But a Long Way to Go. Reduced Effectiveness and Dangers of Reverse Use Dependence," *Circulation* 81:686-690 (1990); Mitcheson et al., "A Structural Basis For Drug-Induced Long QT Syndrome," *Proc. Natl. Acad. Sci. U.S.A.* 97:12329-12333 (2000); Roden et al., "A Plethora of Mechanisms in the HERG-Related Long QT Syndrome. Genetics Meets Electrophysiology," *Cardiovasc. Res.* 44:242-246 (1999), which are hereby incorporated by reference in their entirety]. However, the contribution of $I_{Kr}$ to repolarization during tachycardia, which might also be important for the development of cardiac arrhythmias, has not been well characterized. The observation that reducing $I_{Kr}$ increases the magnitude of APD alternans may provide an additional mechanism to account for the proarrhythmic effects of $I_{Kr}$ blockers, in that increased alternans magnitude would be expected to destabilize ventricular tachyarrhythmias, leading to the development of VF. Conversely, the observation that increasing $I_{Kr}$ reduces the magnitude of APD alternans and the slope of the APD restitution relation provides a rationale for the development of a new class of compounds, $I_{Kr}$ agonists, with the expectation that such compounds may have anti-fibrillatory effects.

The latter hypothesis relies, however, on the expectation that $I_{Kr}$ can be increased sufficiently to reduce the slope of the restitution relation without shortening action potential duration to such an extent that contractility is impaired, secondary to a shortening of the plateau duration and attenuation of $I_{Ca}$. In addition, shortening of APD may lead to a reduction in the wavelength of reentry circuits (where wavelength=refractory period×conduction velocity). Reduction of the wavelength could, in turn, precipitate wavebreak by other mechanisms (e.g., so-called "head-tail" interactions, where a wavefront encounters a waveback and fragments) [Hund et al., "Dynamics of Action Potential Head-Tail Interaction During Reentry in Cardiac Tissue: Ionic Mechanisms," *Am. J. Physiol.* 279: H1869-H1879 (2000), which is hereby incorporated by reference in its entirety]. These and other potential drawbacks to the use of K-channel agonists to suppress VF remain to be evaluated critically.

Until recently, therapy for the prevention of sudden cardiac death has been based on the presumption that frequent ventricular ectopy, in particular ventricular tachycardia, is a prelude to ventricular fibrillation [Myerburg et al., "Life-Threatening Ventricular Arrythmias: the Link Between Epidemiology and Pathophysilogy," In *Cardiac Electrophysiology: From Cell to Bedside* (AZipes, D. P. and Jalife, J. eds), pp. 723-731, WB Saunders Co., Philadelphia (1995), which is hereby incorporated by reference in its entirety]. Accordingly, drugs that suppress inducible or spontaneously occurring ventricular tachycardia are expected to prevent sudden death. However, recent large-scale clinical trials have indicated that classes of drugs that are effective for the suppression of ventricular tachycardia, e.g., Class I and Class III antiarrhythmic drugs, do not prevent sudden death and, in fact, may be proarrhythmic [Waldo et al., "Effect of D-Sotalol on Mortality in Patients With Left Ventricular Dysfunction After Recent and Remote Myocardial Infarction. The SWORD Investigators. Survival with Oral D-Sotalol. *Lancet* 348, 7-12 (1996); Echt et al., "Mortality and Morbidity in Patients Receiving Encamide, Flecamide or Placebo: the Cardiac Arrhythmia Suppression Trial," *New Engl. J. Med.* 324: 781-788 (1991), which are hereby incorporated by reference in their entirety]. In contrast, other classes of drugs that are not particularly effective for the suppression of most forms of ventricular tachycardia, such as beta-adrenergic receptor antagonists [Yusuf et al., "Overview of Results of Randomized Clinical Trials in Heart Disease: I. Treatments Following Myocardial Infarction," *J. Am. Med. Assoc.* 260:2088-2095 (1988), which is hereby incorporated by reference in its entirety] and calcium channel antagonists [Held et al., "Impact of Calcium Channel Blockers on Mortality," In *Cardiovascular Pharmacology and Therapeutics* (Singh, B. N. et al., eds), pp. 525-533, Churchill Livingston (1994), which is hereby incorporated by reference in its entirety], may reduce mortality from sudden death.

If a causal relationship between the slope of the APD restitution relation and VF is confirmed, such a result could have significant implications for the pharmacological therapy of sudden cardiac death. Drugs that reduce the slope of the restitution relation would be expected to prevent the development of VF, but would not be expected to suppress ventricular tachycardia, if ventricular tachycardia is caused by some variant of spiral wave reentry. Conversely, drugs that do not reduce the slope of the restitution relation would not be expected to prevent VF, although they might suppress ventricular tachycardia, perhaps via a mechanism that does not involve alteration of restitution kinetics (e.g. slowing of conduction or prolongation of refractoriness).

Given these expectations, the usefulness of existing agents for the prevention of VF could be reevaluated in light of their effects on the restitution relation and new drugs targeted against restitution could be developed. Naturally, such an effort would need to recognize that factors other than APD restitution contribute importantly to the induction and maintenance of VF. Furthermore, drugs intended to alter restitution selectively might have additional effects that could offset their intended effect. Nevertheless, judicious alteration of the APD restitution slope appears to be a promising approach to the treatment of VF and, as such, represents a potentially fruitful opportunity for drug development.

Electrical restitution is a recent addition to factors that play a key role in the development of ventricular tachyarrhythmias. Experimental interventions that reduce the slope of the restitution relation have been effective in suppressing VF. These results encourage further investigation of altering restitution as a means of preventing sudden death, with the realization that clinically useful interventions that flatten restitution without having untoward effects have yet to be developed.

Although the invention has been described in detail for the purposes of illustration, it is understood that such detail is solely for that purpose, and variations can be made therein by those skilled in the art without departing from the spirit and scope of the invention as defined in the claims that follow.

What is claimed is:

1. A system for use in identifying treatment therapies as therapeutic strategies for preventing ventricular tachycardia from developing into ventricular fibrillation, said system comprising:
   a medical device programmed to detect ventricular tachycardia in a subject;
   monitor intervals between electrical stimuli in the heart of the subject;
   determine if an initial 3 stimuli in groups of 4 stimuli from said monitoring in the heart correspond to rest interval values (I) predicted to lead to ventricular fibrillation as defined by a first equation as follows:

$$I_{n+1}(x_i) = \tau + \sum_{j=0}^{i-1} \frac{\Delta x}{c(I_{n+1}(x_j))} - \sum_{j=0}^{i-1} \frac{\Delta x}{c(I_n(x_j))} - D_{n+1}(x_i),$$

wherein τ is a time interval between activations applied to a pacing site $(x_i)$, Δx is 0.1, $I_{n+1}$ $(x_j)$ is a rest interval value of the n+1th action potential at a pacing site $(x_j)$, $I_n$ $(x_j)$ is a rest interval value of an nth action potential at a pacing site $(x_j)$, $D_{n+1}$ $(x_i)$ is an action potential duration of an n+1th action potential at pacing site $(x_i)$, c is a velocity recovery function of $I_n$ $(x_j)$ and $I_{n+1}$ $(x_j)$, respectively;
   identify treatment therapies which prevent occurrence of a fourth stimuli corresponding to the rest interval values; and
   identify treatment therapies which prevent said ventricular tachycardia from becoming ventricular fibrillation as therapeutic strategies for prevention of ventricular fibrillation.

2. The system according to claim 1, wherein said medical device is further programmed to identify one or more electrical impulses.

3. The system according to claim 1, wherein said medical device is further programmed to identify therapies which achieve velocity restitution values as defined by $c(I)=V_{max}(1-\exp(-(I+\beta/\delta))$, wherein $V_{max}$ is maximum velocity which is 0.72, δ is a constant which is 14, and β is a velocity variable which is 7.704 to 30.236 as therapeutic strategies for prevention of ventricular fibrillation.

4. The system according to claim 1, wherein said medical device is further programmed to identify therapies identifies therapies which achieve potential duration values as defined by a second equation as follows:

$$D_{n+1} = f(M_{n+1}, I_n) = (1 - \alpha M_{n+1})\left(A + \frac{B}{1 + e^{-(I_n - c)/\tau_D}}\right)$$

wherein A, B, and C are constants and A is 88, B is 122, C is 40, $M_{n+1}$ is a cardiac memory value of an n+1th action potential, $I_n$ is a rest interval of an nth action potential, $\alpha$ is a memory variable, and $\tau_D$ is a time interval between activations as therapeutic strategies for prevention of ventricular fibrillation.

5. The system according to claim 4, wherein said medical device is further programmed to identify therapies identifies therapies which achieve potential duration values as defined by the second equation and wherein $\alpha$ is 0.58 to 0.8 as therapeutic strategies for prevention of ventricular fibrillation.

6. The system according to claim 4, wherein said medical device is further programmed to identify therapies identifies therapies which achieve potential duration values as defined by the second equation and wherein $\tau_D$ is 32 to 40 ms as therapeutic strategies for prevention of ventricular fibrillation.

* * * * *